(12) United States Patent
Razouki

(10) Patent No.: US 12,264,432 B2
(45) Date of Patent: Apr. 1, 2025

(54) IONIC OXIDATION REFRESHING SYSTEM AND METHOD

(71) Applicant: DRESSFRESH, Inc., Chula Vista, CA (US)

(72) Inventor: Aram Razouki, La Mesa, CA (US)

(73) Assignee: DRESSFRESH, Inc., Chula Vista, CA (US)

( * ) Notice: Subject to any disclaimer, the term of this patent is extended or adjusted under 35 U.S.C. 154(b) by 796 days.

(21) Appl. No.: 17/528,088

(22) Filed: Nov. 16, 2021

(65) Prior Publication Data

US 2022/0072170 A1 Mar. 10, 2022

Related U.S. Application Data

(63) Continuation-in-part of application No. PCT/US2020/032984, filed on May 14, 2020.
(Continued)

(51) Int. Cl.
*A61L 2/22* (2006.01)
*A61L 2/14* (2006.01)
(Continued)

(52) U.S. Cl.
CPC .............. *D06F 58/203* (2013.01); *A61L 2/14* (2013.01); *A61L 2/202* (2013.01); *A61L 2/22* (2013.01);
(Continued)

(58) Field of Classification Search
CPC ........ D06F 58/203; D06F 43/085; A61L 2/14; A61L 2/202; A61L 2/22; A61L 9/013;
(Continued)

(56) References Cited

U.S. PATENT DOCUMENTS 6,134,806 A 10/2000 Dhaemers
6,846,498 B2 1/2005 DeAth et al.
(Continued)

FOREIGN PATENT DOCUMENTS

CN 107261731 A 10/2017
CN 110074308 A * 8/2019 ............... A23L 3/00
(Continued)

OTHER PUBLICATIONS

English translation of He et al. (Year: 2019).*
(Continued)

*Primary Examiner* — Sean E Conley
*Assistant Examiner* — Aham Lee
(74) *Attorney, Agent, or Firm* — Procopio, Cory, Hargreaves & Savitch LLP

(57) ABSTRACT

An ionic oxidation refreshing system for refreshing an odorized item, comprising an enclosure with an airflow system to contact the odorized item on all sides; an ionization system that produces a positively charged ionized ozone gas mixture inside of the enclosure, killing germs, including odor-causing bacteria, viruses, molds, and fungus, and provides the odorized item inside the enclosure with a net positive charge; a filter that neutralizes and filters out any toxic by-products; an electrostatic liquid atomization system that creates a fine mist of a quick-cleaning solution, and, in conjunction with the airflow system, causes solution droplets to penetrate deep into the odorized item and agitate a surface of the odorized item, ensuring the formula is evenly delivered onto the odorized item without over saturating any area.

19 Claims, 34 Drawing Sheets

Related U.S. Application Data

(60) Provisional application No. 62/849,323, filed on May 17, 2019.

(51) Int. Cl.
| | | |
|---|---|---|
| *A61L 2/20* | (2006.01) | |
| *A61L 9/013* | (2006.01) | |
| *A61L 9/04* | (2006.01) | |
| *A61L 9/20* | (2006.01) | |
| *B01D 46/00* | (2022.01) | |
| *B01D 46/24* | (2006.01) | |
| *B01D 53/78* | (2006.01) | |
| *B01D 53/86* | (2006.01) | |
| *D06F 43/08* | (2006.01) | |
| *D06F 58/20* | (2006.01) | |
| *D06M 11/34* | (2006.01) | |

(52) U.S. Cl.
CPC .............. *A61L 9/013* (2013.01); *A61L 9/04* (2013.01); *A61L 9/205* (2013.01); *B01D 46/0038* (2013.01); *B01D 46/2411* (2013.01); *B01D 53/78* (2013.01); *B01D 53/8621* (2013.01); *B01D 53/8668* (2013.01); *B01D 53/8675* (2013.01); *D06F 43/085* (2013.01); *D06M 11/34* (2013.01); *A61L 2202/11* (2013.01); *A61L 2202/122* (2013.01); *A61L 2202/13* (2013.01); *A61L 2202/14* (2013.01); *A61L 2209/111* (2013.01); *A61L 2209/14* (2013.01); *A61L 2209/212* (2013.01); *B01D 2257/106* (2013.01); *B01D 2257/40* (2013.01); *B01D 2257/708* (2013.01); *B01D 2259/804* (2013.01)

(58) Field of Classification Search
CPC ........ A61L 9/04; A61L 9/205; A61L 2202/11; A61L 2202/122; A61L 2202/13; A61L 2202/14; A61L 2209/111; A61L 2209/14; A61L 2209/212; A61L 2/186; A61L 2209/133; A61L 2/24; A61L 9/015; A61L 9/22; A61L 9/014; A61L 2209/15; A61L 2209/22; B01D 46/0038; B01D 46/2411; B01D 53/78; B01D 53/8621; B01D 53/8668; B01D 53/8675; B01D 2257/106; B01D 2257/40; B01D 2257/708; B01D 2259/804; D06M 11/34; D06M 16/00

See application file for complete search history.

(56) References Cited

U.S. PATENT DOCUMENTS

| | | | |
|---|---|---|---|
| 9,399,834 B1* | 7/2016 | Drake | ............... D06M 11/34 |
| 2008/0159907 A1 | 7/2008 | Joshi et al. | |
| 2014/0105783 A1 | 4/2014 | Levsen et al. | |
| 2014/0193294 A1 | 7/2014 | Kain et al. | |
| 2014/0193296 A1 | 7/2014 | Jurak et al. | |
| 2017/0304474 A1 | 10/2017 | Drake | |
| 2018/0154028 A1 | 6/2018 | Offutt et al. | |

FOREIGN PATENT DOCUMENTS

| | | |
|---|---|---|
| EP | 1330976976 A2 | 7/2003 |
| EP | 2488223 B1 | 1/2019 |
| KR | 1020180010268 A | 1/2018 |
| WO | 2005032664 A1 | 4/2005 |
| WO | 2018106967 A | 6/2018 |
| WO | 2018106967 A1 | 6/2018 |

OTHER PUBLICATIONS

Extended European Search report in European Patent Application No. 20810012.3, dated Feb. 9, 2023.

International Written Opinion related to PCT/US2020/032984 dated Nov. 16, 2021-2021.

* cited by examiner

IONIC OXIDATION REFRESHING SYSTEM AND METHOD

CROSS REFERENCE TO RELATED APPLICATIONS

This application is a bypass continuation in part of PCT application PCT/US2020/032984, filed May 14, 2020, which/and claims priority to U.S. patent application Ser. No. 16/874,006, filed May 14, 2020, and U.S. Provisional Patent Application No. 62/849,323, filed May 17, 2019, all of the above of which are incorporated by reference herein.

FIELD OF THE INVENTION

The present invention relates to ionic oxidation systems and methods for killing germs and eliminating odors in clothes, sporting gear, and the like.

BACKGROUND OF THE INVENTION

The excessive cleaning of clothing, shoes, sports gear, and equipment is a waste of time and resources. Most worn or used items are not very dirty after one use and can be back cleaned, or refreshed, as this term is used herein. These items may be frequently used during the week in workouts or sports games. Since most individuals lead busy daily lives, it is often hard to properly clean and maintain their gear. They have the choice of cleaning it at home, which is time consuming, or taking their gear into a professional facility, which is expensive. This presents a serious problem as many athletes are exposed to germs that can cause severe infections. Sports gear and equipment must be sanitized before every use in order to prevent such occurrences. Another problem identified is the difficulty of laundering workout clothes. Since most items are heavily perspired in, they can develop strong odors that are very difficult to eliminate with home laundry processes. This is from bacteria being trapped deep within fibers and not getting killed by current washing machines. The bacteria continue to thrive within the clothing and when worn again after washing, give off a strong and pungent odor during use. Better cleaning technologies are needed to serve the current market.

To address this problem, people must clean items less frequently to save time and resources. However, this requires them to have a convenient method that allows the use of sports gear and equipment multiple times comfortably, before needing to be fully cleaned. Sports gear and equipment are currently sanitized using chemical sprays and wipes. Athletes can also take their gear into a professional facility for full cleaning. Only professional facilities using industrial appliances can ensure consistent results on a multitude of items. Almost every spot is disinfected on the gear or equipment being cleaned. Most people's current cleaning habits do not properly maintain sporting gear between uses. This leads to excessive germ growth on items that are very hard to eliminate with current at-home methods.

Further, most clothing worn today is usually not dirty after one wear. As such, many people have started wearing clothing multiple times before laundering or dry-cleaning them. This is due to the time required for laundry and costs associated with professional dry-cleaning. New advanced manufacturing methods have also created textiles with silver and other antibacterial coatings. The clothes allow a user to wear them multiple times before being laundered. They work by neutralizing the odor-causing bacteria living on apparel fibers. This is used for certain fabrics that are marketed as easy-care, or wash-free. These individuals are seeking alternative solutions to their laundry pains. The excessive cleaning of their wardrobe costs resources and prematurely degrades items, resulting in a shorter wearable life for the article of clothing.

As for refreshing previously worn clothing, most people resort to just masking any odors with scented sprays such as Febreze®. Others may use a dryer or steamer to refresh worn clothing, but the results are not consistent as many odors are tough to remove with only heat and moisture. As such, Dryel® home dryer refreshing kits have been launched to help address this problem. These kits include a special garment bag, spray, and dryer sheets to refresh previously worn clothing in the dryer, helping reduce dry-cleaning bills. Recently, Whirlpool® also launched a 'home dry-cleaning' system called the Swash®, confirming the existence of a real market need. This appliance is designed to quick clean, or refresh, dry-clean only items at home by removing wrinkles, masking odors, and restoring clothing fit using a pod of Tide® water-based solution that is sprayed onto clothing inside and heated. Other recent solutions include steam refreshing closets launched by LG® and Samsung®. These appliances are very large and require professional installation. They are designed to maintain previously worn dress clothing placed inside of the closet by using steam to remove odors and wrinkles.

Most current solutions to the identified problems require more time and money on the customers' part then they would like to invest. Hand cleaning items is a tedious chore to do often. It is not typically recommended to wash sports gear and get it wet. To clean shoes, sports gear, and equipment, people usually use a disinfectant such as Lysol®. The user must individually spray or wipe each item, and let it air dry. This is very time consuming and usually not done often. A person is also limited to the areas they can clean with any sprays or wipes. Harder to reach spots, such as the inside of a glove or shoe, never get sanitized very well. Therefore, it is hard to get good deodorizing results with hand cleaning items. Many athletes note odors returning within hours of application and cleaning. This is due to the improper cleaning of items, leading to bacteria regrowth in hard to reach spots. Germs stay deep within fibers, which degrades materials faster and gives off bad odors, reducing the items usable life. Maintaining gear between uses prevents the growth of germs deep within fibers and protects costly sports gear.

Laundry is also a time-consuming chore that uses a great deal of chemicals, water, and energy to clean clothing. Excessive cleaning of clothing also prematurely wears them down and reduces their usable life. Many articles of clothing sold today are not able to hold their shape or fit after being laundered a few times. Downy® fabric softeners and dryer sheets are marketed as a protectant for clothing fibers, helping them hold shape and stay looking newer, longer. This has resulted in the handwashing of more delicate items, including dry-clean only items, to reduce excessive wear and tear from cleaning. However, this does not kill germs or tough odors set deep within fibers. Special laundry detergents must also be used for sports apparel in order to kill tough odors and bacteria. Other clothing with advanced coatings or treatments, such as silver nanoparticles, get stripped off the fibers by laundry processes and dry-cleaning. These particles are also dangerous pollutants that end up in water sources and are very hard to filter out. Hand-held steamers are also a popular option for refreshing worn clothes but are difficult to use. These devices do not deliver consistent results as some odors cannot be removed using steam, becoming worse from the moisture introduced. They also do not effectively kill germs as the hot steam rapidly cools down by the time it contacts the item. Other home solutions to refresh clothing have been limited by their design and results delivered have been inconsistent. For example, a home dryer refreshing kit requires multiple steps by the user. Items are first sprayed with a pre-treatment, and then placed inside a special garment bag with dryer sheets. The dryer is then run for up to thirty minutes to refresh the items inside. Users have noted mixed feedback on the results as they cannot kill strong odors from body sweat or cigarette smoke, and set in any stains because of the heat used. Home systems, such as the Swash®, try to address these problems with a stand-alone appliance for refreshing clothes. The system has had limited adoption as it is a large appliance and can be difficult to use. A person must properly load items inside with tension clips to obtain good results. These solutions also do not kill any germs or sanitize the clothing from previous use. Since most of these solutions also use moisture to remove wrinkles and mask odors, any germs living inside the clothing fibers will thrive, such as the bacteria found in sweat. More recent steam closet appliances have also had limited adoption due to their price and size. These systems are designed to refresh clothing slowly using steam over a long period of time and cannot be used on a wide range of items. Professional services, such as dry cleaners for clothes, or equipment cleaning facilities for sports gear, require the person to arrange for drop-off and pick-up of their items. Most of the services deliver good and consistent cleaning results for a range of items. However, they are expensive to use often and are becoming an uneconomical option due to increasing prices.

As such, new consumer alternatives are starting to enter the market. These small appliances or portable bags employ ozone technology to eliminate odors and kill germs on used items. Other systems include larger stand-alone appliances with built-in ozone modules. These devices take advantage of activated oxygen to deodorize the items placed inside through oxidation. Currently, they are marketed towards hunters and athletes who have gear that needs deodorizing and sanitizing. They have had limited success due to their size and process. Many systems cannot effectively clean all sides of an item, such as the interior folds of clothing, especially when many items are placed inside. This presents a problem as an item will smell clean on one side, but dirty on the other. These appliances also do not leave behind a fresh scent after cleaning. Users have noted a strong odor left behind from cleaning some items. This is partly due to the oxidation of certain manufactured materials inside, such as plastics or dyed synthetic textiles, off gassing, releasing Volatile Organic Compounds (VOCs) and aldehydes, that are not filtered out. The creation of ozone gas from these systems also forms nitric acid inside which is toxic. These systems leave users with partially cleaned items and pungent odors at times, resulting in a poor user experience that is not easily adopted. Since users do not consistently open the bag or enclosure to a clean aroma, they do not always believe the items inside have been cleaned. Consumers are looking for a convenient method of refreshing many different items at home and on-the-go, with a better user experience that delivers more consistent results.

SUMMARY OF THE INVENTION

The ionic oxidation refreshing system and method, according to an aspect of the present invention, delivers quick and consistent results on items such as clothing, shoes, sports gear, equipment, and many other items that may need refreshing. This process uses ionic oxidation to kill germs and eliminate odors on the surface of items placed inside the enclosure. It begins with the working stage, or ionizing stage, by using a catalyzed corona discharge device to ionize air inside of the enclosure. The device generates a partially ionized cold plasma region on the element to create a supercharged gas mixture containing ionized ozone. A metal catalyst is placed beside and/or coated on the element in proximity to the plasma field region that creates an increased concentration of ions and free radicals when oxidized that potentiate the ozone gas mixture to a higher oxidative power. The gaseous mixture is circulated inside by means of a fan and airflow system. The airflow system may have different configurations but allows for all sides of an item to be treated during the process by increasing the total effective surface area coming into contact with the gas. This supercharged airflow kills microorganisms it encounters on the surface of any items, effectively eliminating any odors as well. By killing the germs and odors on an item, it feels refreshed to the user and comfortable to wear again. For safety, consistent process performance, and an enhanced user experience, a quick cleaning filter cartridge (e.g., gel polymer catalyst formula) is used in the finishing, or filtering, stage. This neutralizes and filters out any toxic by-products from the process, such as ozone, nitric acid, aldehydes, and VOCs. It also leaves behind a fresh scent in the enclosure at the end of a cycle. A user opens the bag to a clean smell and finds the items inside refreshed and ready to use again. This is important as most human beings today relate cleanliness to a clean aroma. When the user opens the enclosure to a fresh scent, their mind triggers into appreciating the items inside have been cleaned and are ready to use again. The ionic oxidation refreshing system and method uses a combination of an ionized ozone gas mixture and a quick cleaning filter cartridge to deliver consistent results across a multitude of items. This is accomplished with a two-stage process run during every cycle. The first stage generates a gaseous mixture of ions, free radicals, and potentiated ozone, also referred to as ionized ozone in this disclosure. This gas is circulated throughout the enclosure to clean items placed inside through surface oxidation. The second stage then runs this charged air filled with process by-products through the filter cartridge until the cycle is complete. This cartridge contains a gel polymer scrubbing formula that is reacted away to neutralize any remaining gases. The formula includes compounds that scrub out process by-products such as ozone, nitric acids, aldehydes, and VOCs that may be leftover or formed in the enclosure by the process. Each cartridge is scented with essential oil-based fragrances that leave behind a fresh scent at the end of a refreshing cycle. An anion diffuser charges scent molecules to help them adhere to items inside more easily. This cartridge is required to ensure a more consistent user experience and works as a process filter after the first stage. The use of a catalyst with the corona discharge device creates a high electric flux density of charged ions and free radicals that combine with ozone to potentiate the overall gas mixture to a higher oxidative power. This greatly increases the cleaning power of this process compared with other systems that rely on ozone gas alone. The power of these oxidizers is boosted from this catalyst by creating an intermediary stage of radical ions in the superoxide gaseous mixture. Instead of using higher concentrations of ozone for longer periods of time, which has a larger chance of damaging items from oxidation shock, lower concentrations of this gaseous mixture can deodorize and sanitize items better and faster than other current systems. The enclosure also employs the use of an airflow system to refresh items more effectively. This allows for all sides of an item to be treated inside of the enclosure using special hardware designs, ensuring more consistent process results on various items placed inside. The system is used to maintain items, such as clothing and gear, between uses. A combination of this ionized ozone process with steam can be implemented in larger appliances for refreshing clothing, by removing wrinkles in addition to odors. This protects the user's investment and extends the usable life of items by reducing excessive cleaning. A refreshing system is used as a preventative measure against germ growth on items, allowing multiple wears or uses comfortably.

Another aspect of the invention involves an ionic oxidation refreshing system for refreshing odorized items, comprising an enclosure to contact the odorized items; an ionizing stage mechanism that produces an ionized ozone gas mixture inside of the enclosure, killing germs, including odor-causing bacteria, viruses, molds, and fungus; and a filtering stage mechanism that neutralizes and filters out any toxic by-products including one or more of ozone, nitric acid, aldehydes, and VOCs resulting from surface oxidation of the odorized items by the ionized ozone gas mixture.

One or more implementations of the above aspect of the invention involves one or more of the following: the ionizing stage mechanism includes a catalyzed corona discharge device containing a hybrid generating element comprising ceramic with a glass glaze coating of ruthenium and metal paste to ionize the air inside of the enclosure; the ionizing stage mechanism includes a metal catalyst adjacent to and/or coated on the catalyzed corona discharge device or generating element that in combination create a high electric flux density of charged ions and free radicals that combine with ozone to potentiate the overall gas mixture to a higher oxidative power; an airflow system to circulate the ionized ozone gas mixture inside the enclosure and provide for air flow on all sides of the odorized items; the enclosure includes a floor and the airflow system includes a raised floor assembly that is raised relative to the floor of the enclosure so that airflow is also provided on an underside of the odorized items; the airflow system further includes a bottom base that rests on the floor of the enclosure, and a plurality of vertical supports that space the raised floor assembly above the bottom base, the raised floor assembly including a plurality of holes that allow air flow there through; the filtering stage mechanism includes a quick cleaning filter cartridge; the quick cleaning filter cartridge includes a gel polymer catalyst formula that neutralizes any remaining toxic gases; the quick cleaning filter cartridge includes an essential oil-based fragrance that releases scent molecules; an anion diffuser that charges the scent molecules to assist in the adherence of the scent molecules to the odorized items in the enclosure; the quick cleaning filter cartridge includes a cartridge solution having gel or liquid formula, and scrubbing compounds; the scrubbing compounds include one or more of a blend of metal nanoparticle solutions, manganese oxide solutions, salt solutions, sodium bicarbonate solutions, silicon dioxides, hydroxides, and peroxides; a module housing the ionizing stage mechanism and the filtering stage mechanism; the module is configured to wirelessly connect with a smart device to control operation of the module; the module is powered by at least one of a rechargeable battery and an AC adapter; the enclosure includes an interior liner that is resistive to oxidation shock and inert to an ionic oxidation refreshing process therein; the enclosure is a member from the group consisting of: duffel bag, backpack, suitcase, plastic bin, locker unit, garment bag, closet system, laundry hamper, and a stand-alone appliance; the enclosure may employ the use of steam in the filtering stage to remove wrinkles from clothing placed inside; one or more sensors to process input to help monitor enclosure conditions and adjust generating times for maintaining optimal gas concentrations for better cleaning performance; and/or the ionic oxidation refreshing system includes a smart control setting to adjust process stages from the inputs of the one or more sensors in real time, during a cycle run.

Another aspect of the invention involves a method of using the ionic oxidation refreshing system of the aspect of the invention described most immediately above, comprising producing an ionized ozone gas mixture inside of the enclosure with the ionizing stage mechanism so that the items inside of the enclosure have a net positive surface charge; neutralizing and filtering out with the filtering stage mechanism any toxic by-products including one or more of ozone, nitric acid, aldehydes, and VOCs resulting from surface oxidation of the odorized items by the ionized ozone gas mixture, and charging scent molecules with a net negative charge, opposite the net positive charge of the items inside of the enclosure, facilitating the adherence of scent molecules to the items inside of the enclosure.

An implementation of the above method aspect of the invention involves producing an ionized ozone gas mixture inside of the enclosure and includes staggering the producing of the ionized ozone gas mixture inside of the enclosure so as to maintain a predetermined concentration of the ionized ozone gas mixture inside of the enclosure during the ionizing stage.

A still further aspect of the invention involves an ionic oxidation refreshing system for refreshing an odorized item comprising an enclosure with an airflow system to contact the odorized item on all sides; an ionization system that produces a positively charged ionized ozone gas mixture inside of the enclosure, killing germs, including odor-causing bacteria, viruses, molds, and fungus, and provides the odorized item inside the enclosure with a net positive charge; a filter that neutralizes and filters out any toxic by-products; an electrostatic liquid atomization system that creates a fine mist of a quick-cleaning solution, and, in conjunction with the airflow system, causes solution droplets to penetrate deep into the odorized item and agitate a surface of the odorized item, ensuring the formula is evenly delivered onto the odorized item without over saturating any area.

One or more implementations of the aspect of the invention described immediately above includes one or more of the following: the airflow system includes a plurality of movable high-speed air blades that deliver air blade streams of the fine mist of quick-cleaning solution, the high-speed air blades configured to create surface tension on the odorized item to smooth and stretch out any wrinkles; one or more of the plurality of movable high-speed air blades are vertically movable; the airflow system is configured so that the fine mist of quick-cleaning solution is delivered within the air blade streams; the filter is configured to neutralize and filter out any toxic by-products including one or more of ozone, nitric acid, aldehydes, and VOCs resulting from surface oxidation of the odorized item, and charging scent molecules with a net negative charge to adhere to the item inside; the filter includes a quick cleaning filter cartridge with an anion diffuser; the quick cleaning filter cartridge includes a catalytic oxidation polymer formula that neutralizes any remaining toxic gases; the quick cleaning filter cartridge includes an essential oil-based fragrance that releases scent molecules; the anion diffuser is configured to charge the scent molecules with a net negative charge, to assist in the adherence of the scent molecules to the positively charged items in the enclosure; the quick cleaning filter cartridge includes a cartridge solution having a polymer oxidation catalyst formula with scrubbing compounds; the scrubbing compounds include one or more of manganese oxide solutions, salt solutions, sodium bicarbonate solutions, silicon dioxides, hydroxides, and peroxides; an ultrasonic hanger configured to agitate the odorized item at a high frequency; the airflow system includes a high-speed centrifugal blower that powers the plurality of air blades, which are located in front, behind, and/or below the odorized item; an internal camera configured to detect at least one of the odorized item and a material of the odorized item; a RFID reader configured to read garment tag care instructions to adjust process parameters; a heater configured to rapidly dry the odorized item; the ionizer includes a catalyzed corona discharge device containing a hybrid generating element comprising of ceramic with a quartz glass glaze coating or comprising of stainless steel with a ruthenium metal paste coating to ionize the air inside of the enclosure; the ionizer includes a metal catalyst, the metal catalyst being one of copper, nickel, aluminum, or other metals which have a net positive charge and release cations by oxidation, the metal catalyst also being one of adjacent to the catalyzed corona discharge device and coated on the generating element, creating a high electric flux density of charged ions and free radicals that combine with ozone to potentiate it to ionized ozone gas, with a higher oxidative power.

An additional aspect of the invention involves a method of using the ionic oxidation refreshing system of the aspect of the invention described most immediately above comprising: producing an ionized ozone gas mixture inside of the enclosure with the ionization system so that the odorized item inside of the enclosure has a net positive charge; delivering the quick-cleaning solution with the electrostatic liquid atomization system and the airflow system so that the fine mist of the quick-cleaning solution penetrates deep into the odorized item and agitates the surface of the odorized item, ensuring the formula is evenly delivered onto the odorized item without over saturating any area; neutralizing and filtering out with the filter any toxic by-products resulting from surface oxidation of the odorized item by the ionized ozone gas mixture, and charging scent molecules with a net negative charge, opposite the net positive surface charge on the odorized item inside of the enclosure, facilitating the adherence of scent molecules to the items inside of the enclosure.

One or more implementations of the aspect of the invention described immediately above includes one or more of the following: the airflow system includes a plurality of movable high-speed air blades, and delivering the quick-cleaning solution includes delivering the quick-cleaning solution with the electrostatic liquid atomization system and the plurality of movable high-speed air blades so that surface tension is created on the odorized item to smooth and stretch out any wrinkles; the plurality of movable high-speed air blades are vertically movable; the airflow system is configured so that the fine mist of quick-cleaning solution is delivered within the air blade streams; the filter is configured to neutralize and filter out any toxic by-products including one or more of ozone, nitric acid, aldehydes, and VOCs resulting from surface oxidation of the odorized item, and charging scent molecules with a net negative charge to adhere to the item inside; the filter includes a quick cleaning filter cartridge with an anion diffuser; the quick cleaning filter cartridge includes a catalytic oxidation polymer formula that neutralizes any remaining toxic gases; the quick cleaning filter cartridge includes an essential oil-based fragrance that releases scent molecules; the anion diffuser is configured to charge the scent molecules with a net negative charge, to assist in the adherence of the scent molecules to the positively charged items in the enclosure; the quick cleaning filter cartridge includes a cartridge solution having a polymer oxidation catalyst formula with scrubbing compounds; the scrubbing compounds include one or more of manganese oxide solutions, salt solutions, sodium bicarbonate solutions, silicon dioxides, hydroxides, and peroxides; an ultrasonic hanger configured to agitate the odorized item at a high frequency; the airflow system includes a high-speed centrifugal blower that powers the plurality of air blades, which are located in front and behind the odorized item; an internal camera configured to detect at least one of the odorized item and a material of the odorized item; a RFID reader configured to read garment tag care instructions to adjust process parameters; a heater configured to rapidly dry the odorized item; the ionizer includes a catalyzed corona discharge device containing a hybrid generating element comprising of ceramic with a quartz glass glaze coating or comprising of stainless steel with a ruthenium metal paste coating to ionize the air inside of the enclosure; the ionizer includes a metal catalyst, the metal catalyst being one of copper, nickel, aluminum, or other metals which have a net positive charge and release cations by oxidation, the metal catalyst also being one of adjacent to the catalyzed corona discharge device and coated on the generating element, creating a high electric flux density of charged ions and free radicals that combine with ozone to potentiate it to ionized ozone gas, with a higher oxidative power.

BRIEF DESCRIPTION OF DRAWINGS

The accompanying drawings, which are incorporated in and form a part of this specification illustrate embodiments of the invention and together with the description, serve to explain the principles of the invention.

DESCRIPTION OF EMBODIMENT OF THE INVENTION

Figure 1A:
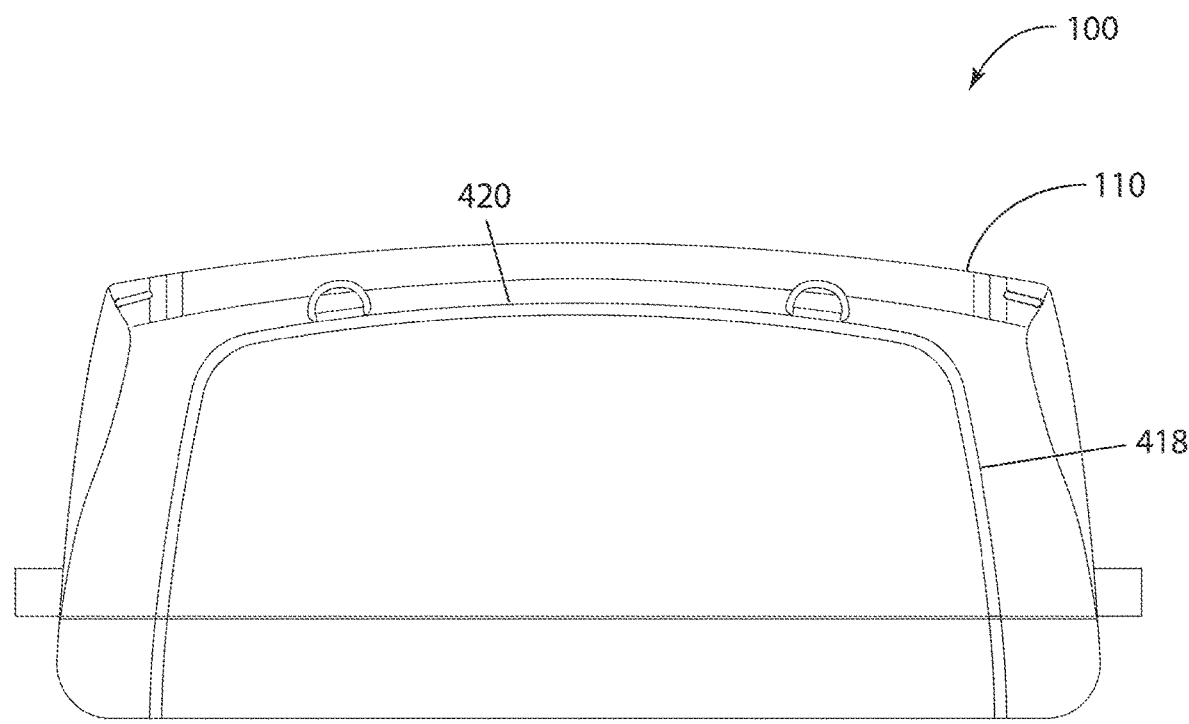
FIG. 1A is a front side elevational view or plain side view of an embodiment of a sports gym bag that may be used as an exemplary air-tight enclosure for the ionic oxidation refreshing system and method.
Figure 1B:
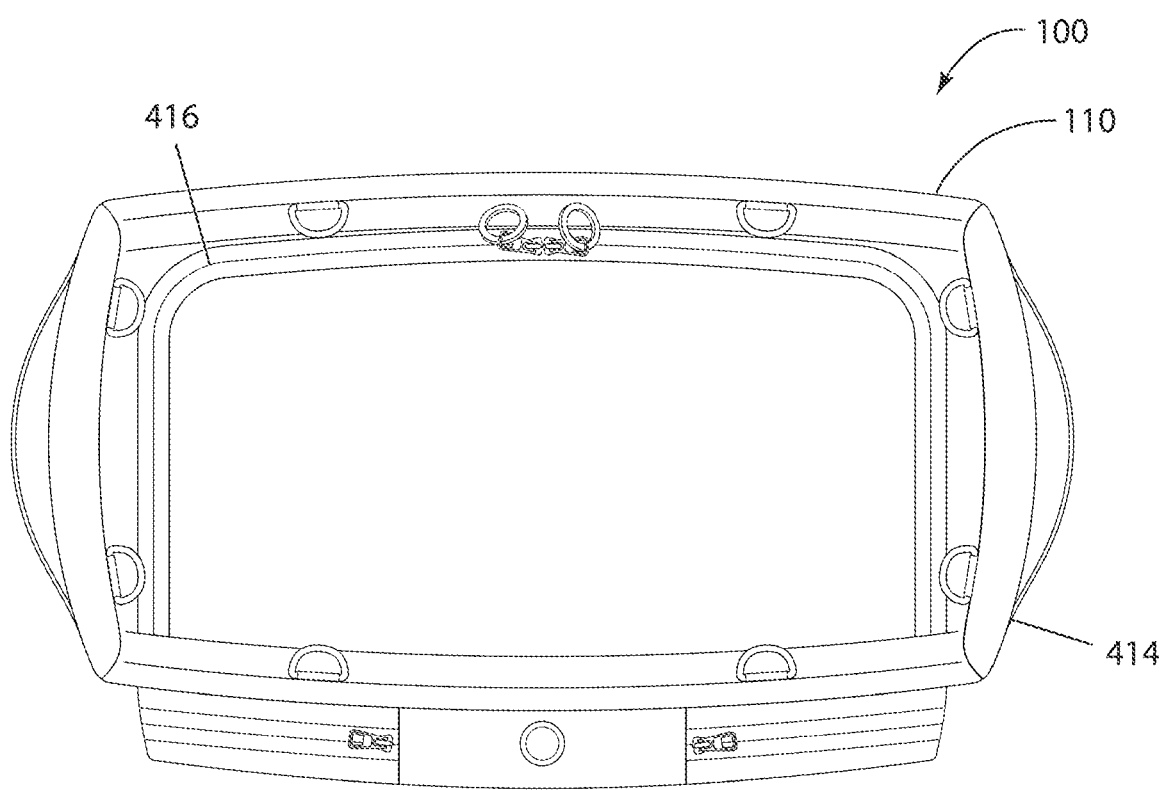
FIG. 1B is a top plan view or top view of the sports gym bag of FIG. 1A.
Figure 1C:
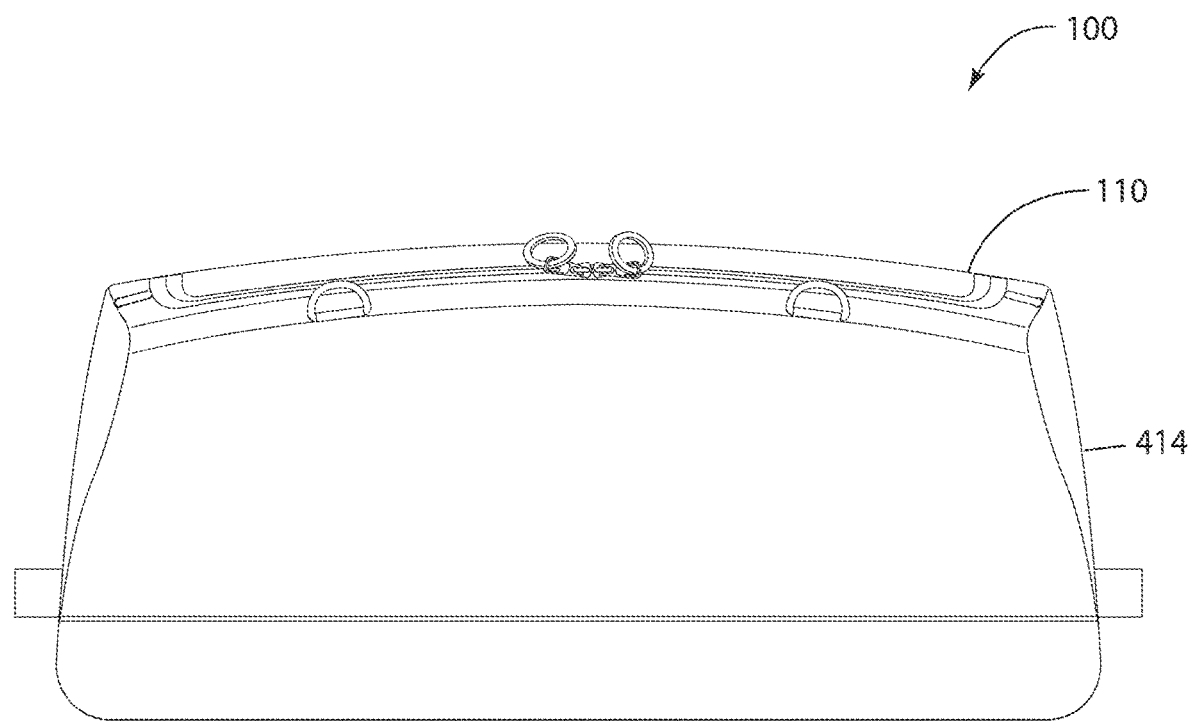
FIG. 1C is a rear side elevational view or pocket side view of the sports gym bag of FIG. 1A.
Figure 1D:
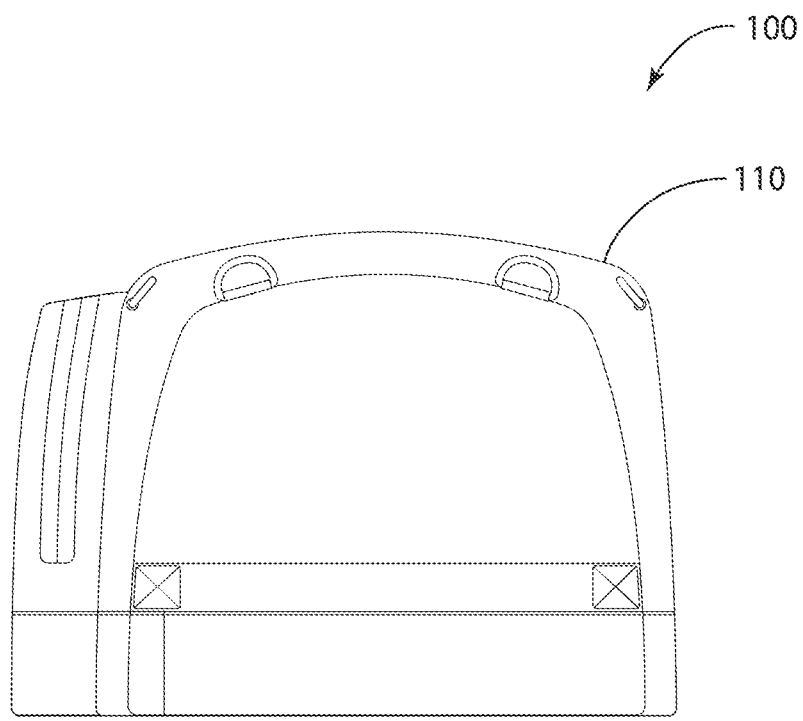
FIG. 1D is a right elevational view or right-side view of the sports gym bag of FIG. 1A.

With reference to FIGS. 1A-9, an embodiment of an ionic oxidation refreshing system 100 and method will be described. Although the ionic oxidation refreshing system 100 and method will be shown and described primarily with respect to a sports gym bag 110 as an exemplary air-tight enclosure 130, in alternative embodiments, other types of air-tight enclosures may include, but not limited to, duffel bags, backpacks, suitcases, plastic/storage bins, laundry baskets, lockers, garment bags, closets and stand-alone appliances.

The ionic oxidation refreshing system 100 and method (also referred to as Ionic Oxidation Refreshing (IOR) process) kills germs and eliminates odors on previously used items (e.g., clothing, shoes, sports gear, and many other items that may require refreshing or sanitizing after use). The system 100 and the IOR process uses a combination of ions, free radicals, potentiated ozone (supercharged activated oxygen) and a quick cleaning filter cartridge (e.g., gel-based formula cartridge or liquid-based formula cartridge) to quick clean previously worn items. The IOR process is delivered via an electronic module inside enclosures designed for various customer needs. This process can eliminate almost all germs and odors on items, while leaving behind a fresh scent. These smart cycles use preset, lab created stages, in short time frames. The preprogrammed cycles are developed for each enclosure and ensure specific gas concentrations are reached inside for a set period to deliver an effective kill rate for germs found on commonly worn items, such as sports gear and apparel.

The system 100 includes the following hardware components: an electronic module 120 with ionization devices; an enclosure 130 with built-in airflow system; and a quick cleaning filter cartridge (e.g., gel-based formula or liquid-based formula) ("cartridge") 170. Each of these will be discussed in turn below.

With reference to FIGS. 2A-2F, the electronic module 120 ionizes air inside of the enclosure 130 by generating a partially ionized cold plasma that is catalyzed to create a supercharged gaseous mixture. The ionized ozone gas mixture is discharged from the module 120 into a specialized airflow system 150 inside of the enclosure 130 (e.g., sports gym bag 110). The airflow system 150 is built within the base or walls of the enclosure housing. Its design maximizes airflow around everything being refreshed and allows for all sides of items to be treated simultaneously. This ensures items do not need to be flipped or rotated inside during a cycle and maintains more consistent process results.

The module 120 is a high-tech device developed specifically for delivering the IOR process inside the enclosure 130. The module 120 houses a corona discharge generating element 160, gas generator transformer 162, cation catalyst 164, the filter cartridge 170, an anion diffuser/diffusing fan 180, anion generator transformer 182, a circulating/blower fan 190, rechargeable battery bank/battery 200, and wireless control/PCB/electronics 210. The cartridge 170 is insertable/removable with respect to cartridge slot/holder 220. When fully inserted into the cartridge slot/holder 220, the cartridge 170 actuates cartridge contact switch 230. Air enters the module 120 through air intake vents 240 and exits the module 120 through output vent 250.

Figure 2A:
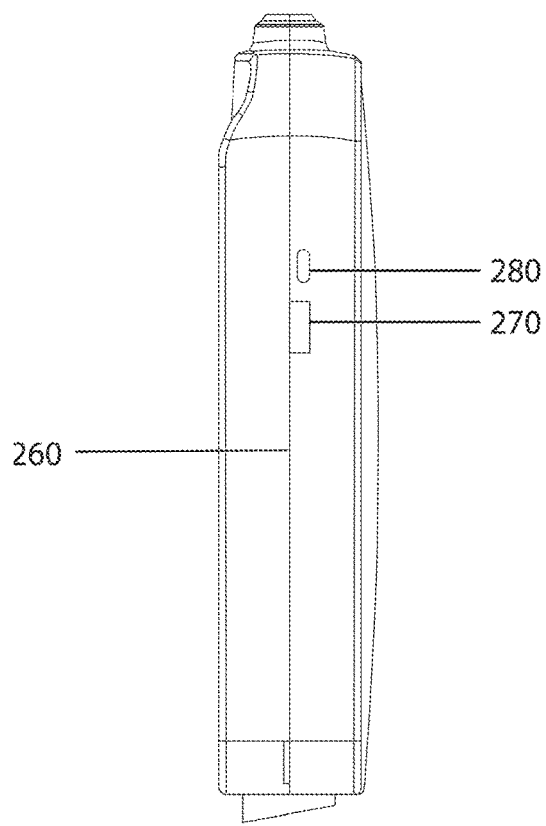
FIG. 2A is front perspective view of an embodiment of a module for the sports gym bag of FIGS. 1A-1F.

With reference to FIG. 2A, a first side 260 of the module 120 includes USB and USB-C charger ports 270, 280. A charger plugs into the charger port 280 for fast charging the rechargeable battery bank/battery 200. One may charge their smart device (e.g., smartphone, smartwatch, wireless headphones, mobile computing device) via the USB port 270.

Figure 2B:
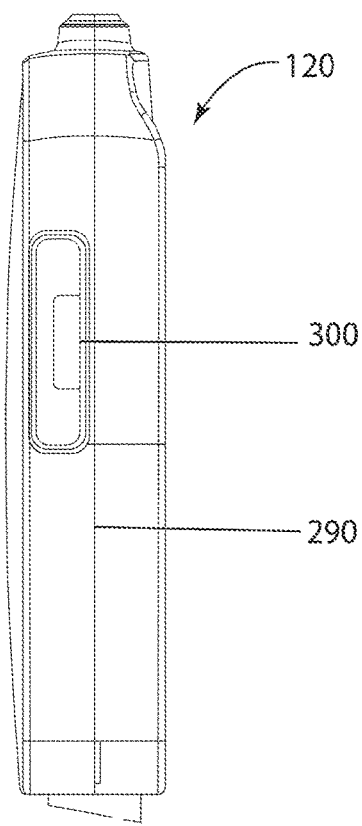
FIG. 2B is a rear perspective view of the module of FIG. 2A.
Figure 2C:
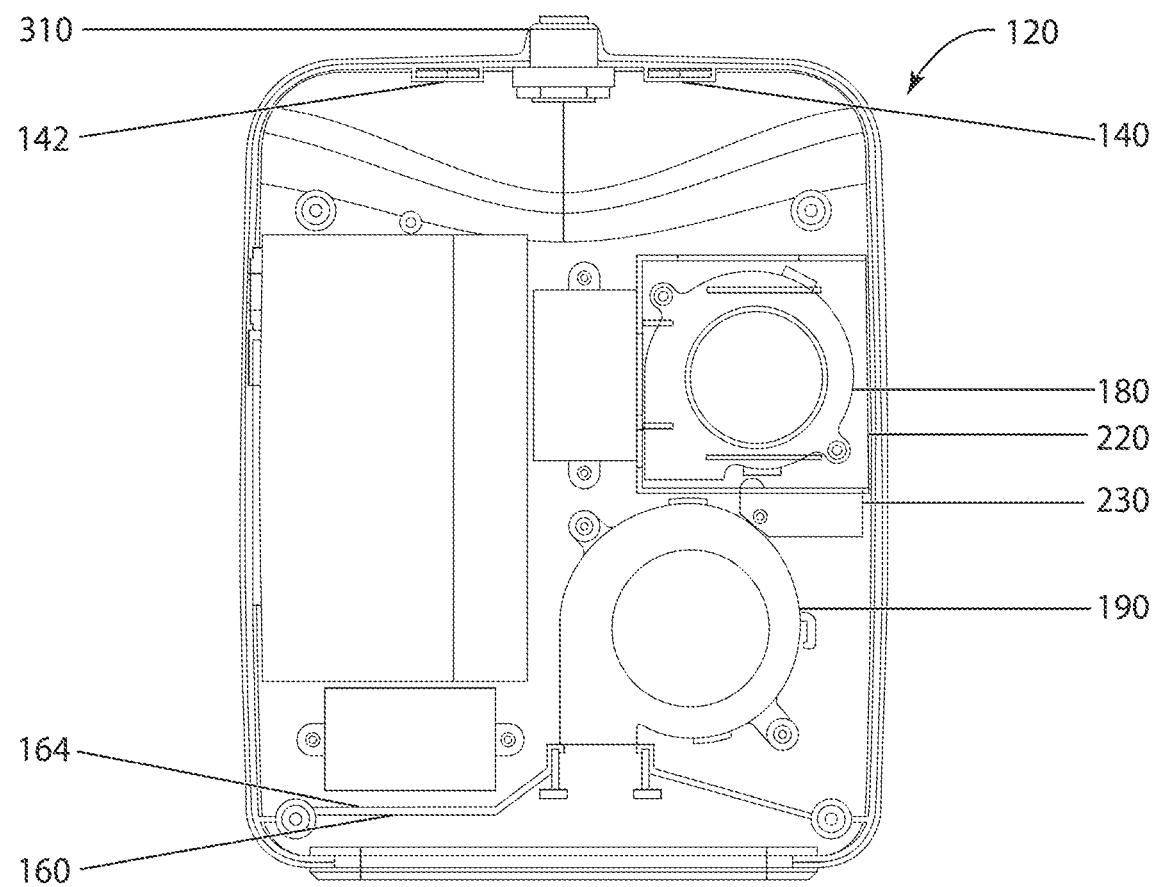
FIG. 2C is a front elevational view of the module of FIG. 2A with the front cover removed to expose an embodiment of module components.
Figure 2D:
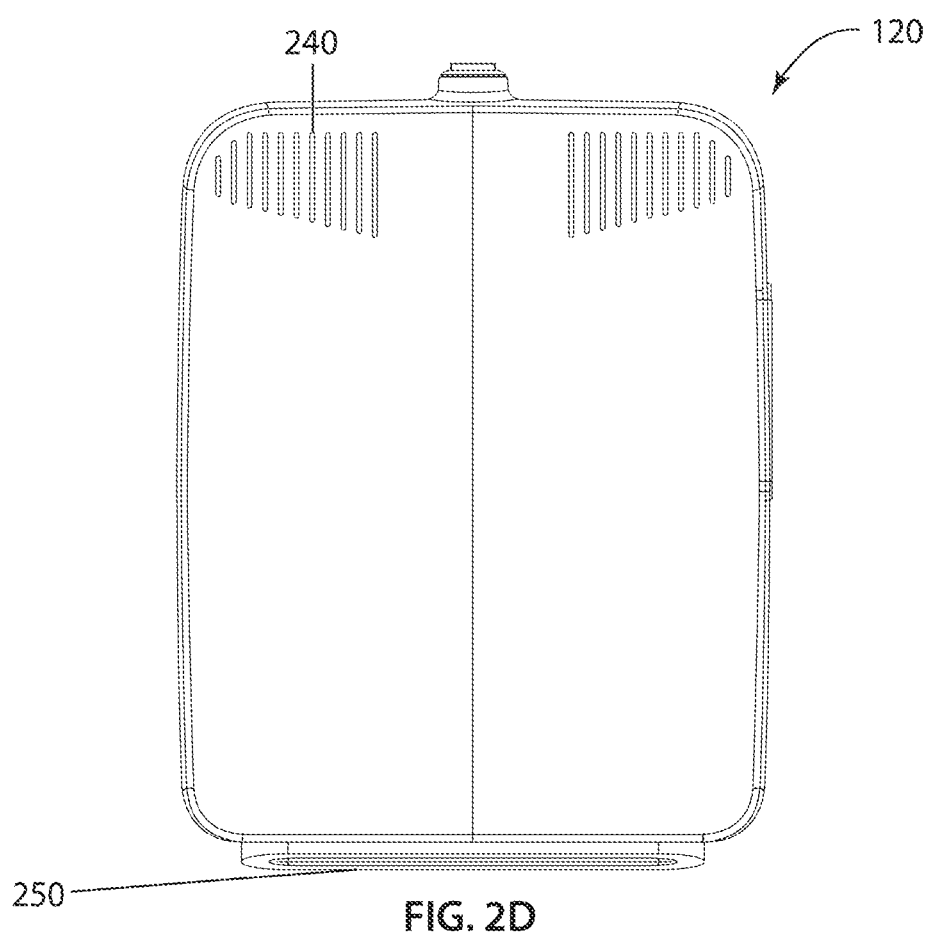
FIG. 2D is a rear elevational view of the front cover of the module of FIG. 2A.
Figure 2E:
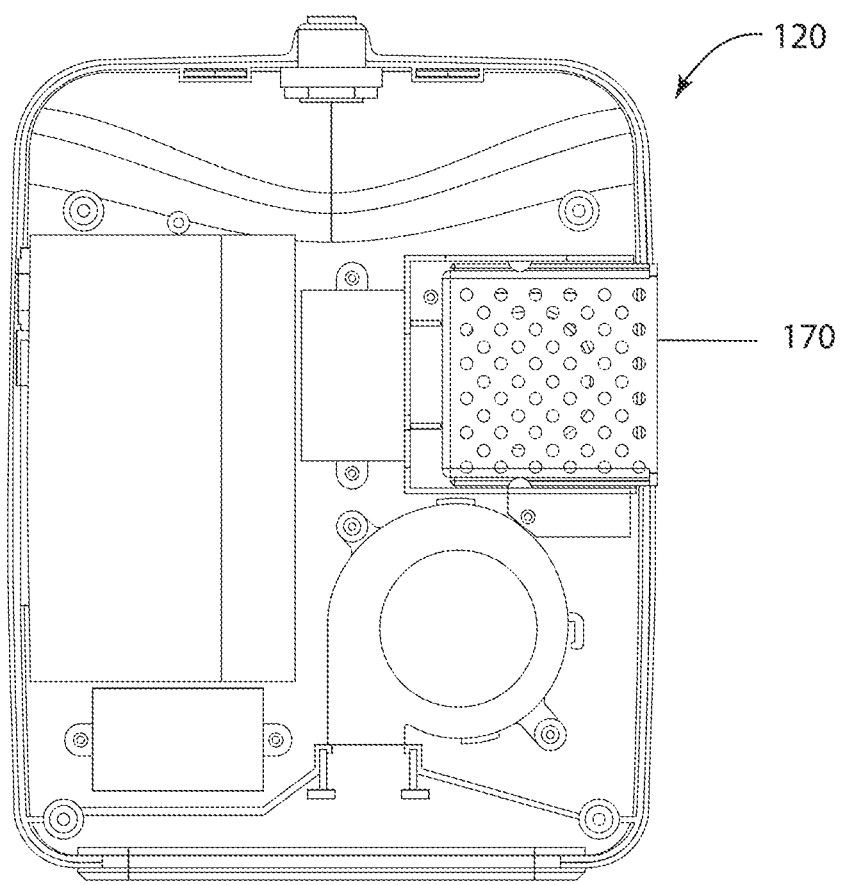
FIG. 2E is another front elevational view of the module of FIG. 2A with the front cover removed to expose an embodiment of module components.
Figure 2F:
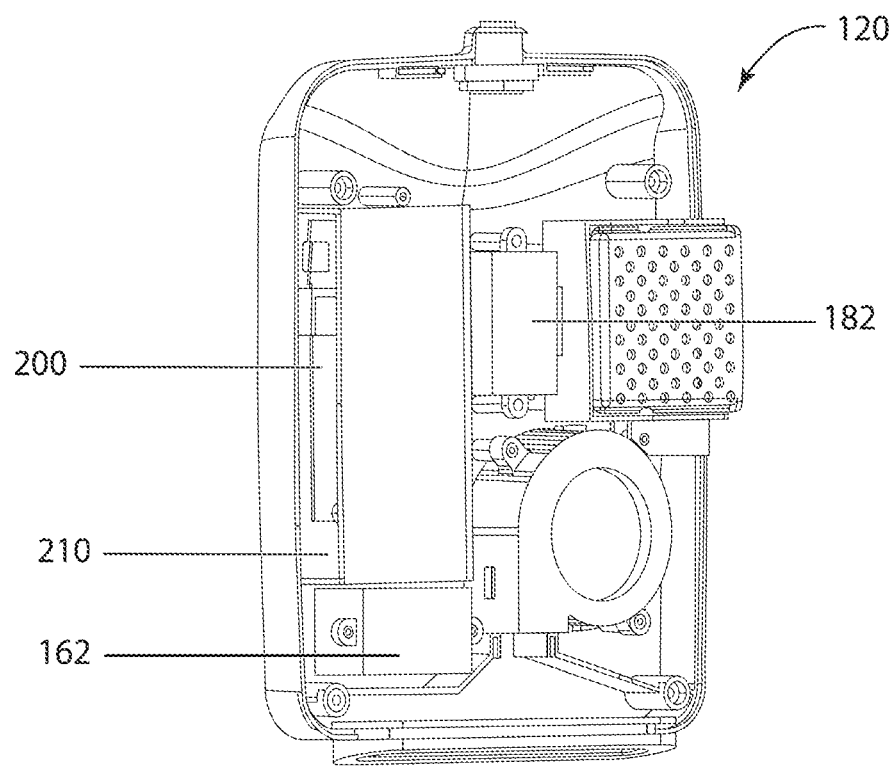
FIG. 2F is a perspective view of the module of FIG. 2A with the front cover removed to expose an embodiment of module components.
Figure 2G:
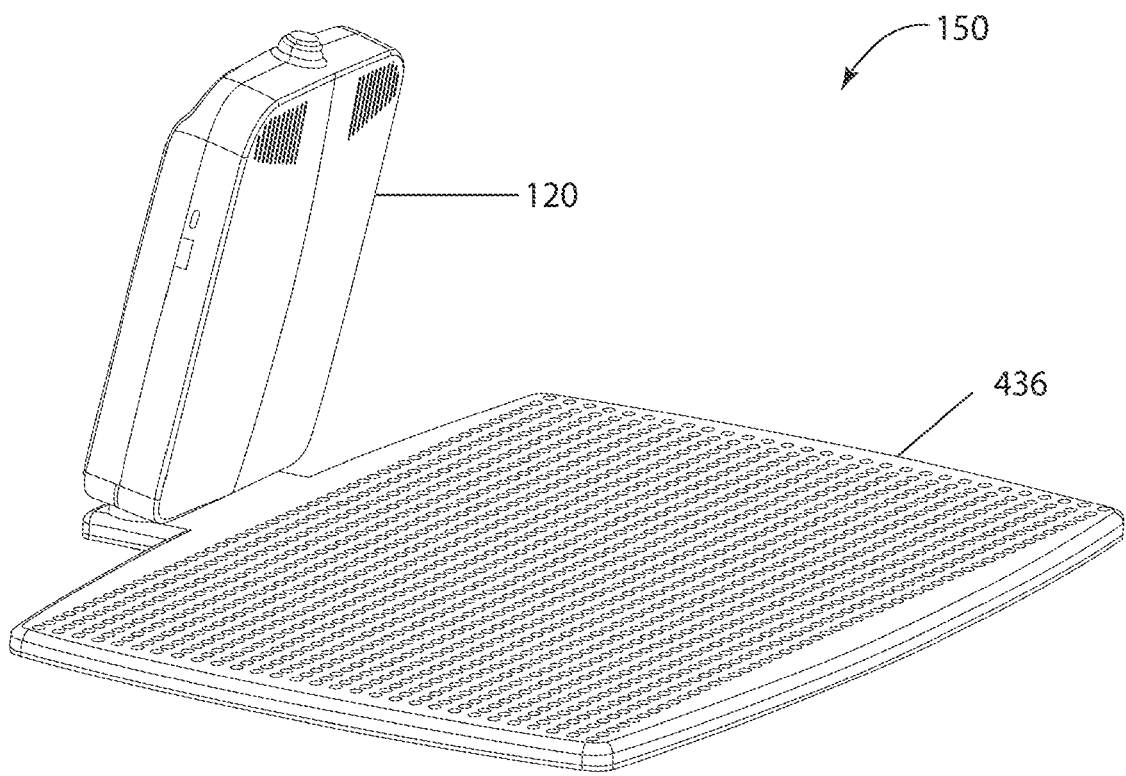
FIG. 2G is a side elevational view of the module and shows the airflow base and raised floor for the airflow system.
Figure 3A:
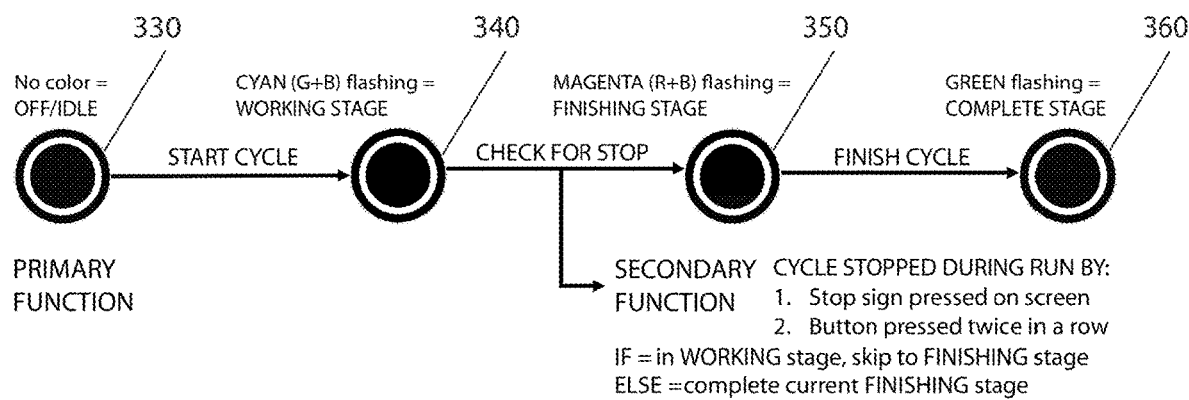
FIG. 3A is an exemplary cycle firmware flowchart with RGB button color map for the module of FIGS. 2A-2F.
Figure 3B:
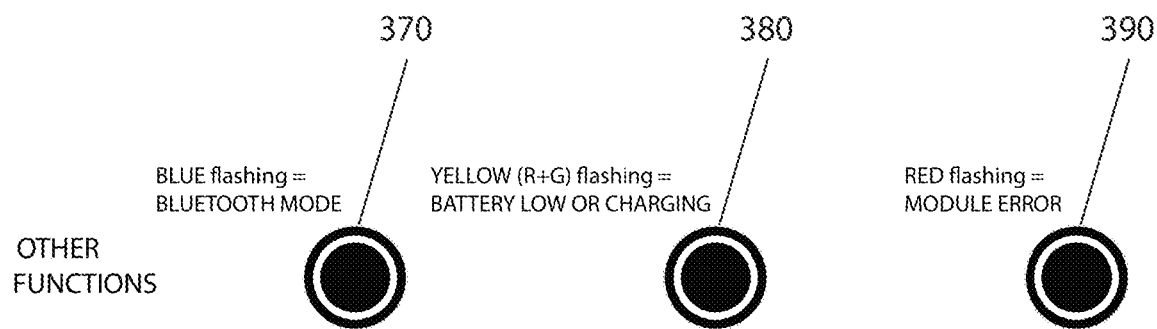
FIG. 3B is an exemplary cycle firmware RGB button color map for the module of FIGS. 2A-2F.

With reference to FIG. 2B, a second side 290 of the module 120 includes hole or displaceable cartridge door 300 for inserting/removing the cartridge 170 into/from the cartridge slot/holder 220.

With reference to FIGS. 2B, 2C, 3A, and 3B, an RGB LED push button 310 is disposed in the top 320 of the module 120. The RGB LED push button 310 has no color in module off/idle condition 330, is cyan (green+blue) flashing in a module working stage condition 340, is magenta (red+blue) in a finishing stage condition 350, and is green flashing in a complete stage condition 360. The primary function of the RGB LED push button 310 is to stop the cycle during run by pressing the RGB LED push button 310 two times in a row. After pressing the RGB LED push button 310 two times in a row, if the module 120 is in a working stage/condition, the module 120 will skip to the finishing stage, otherwise, the finishing stage will be completed. The RGB LED push button 310 is blue flashing in a Bluetooth® mode/condition 370, is yellow (red+green) flashing in a battery low or charging mode/condition 380, and is red flashing in a module error mode/condition 390.

Figure 7A:
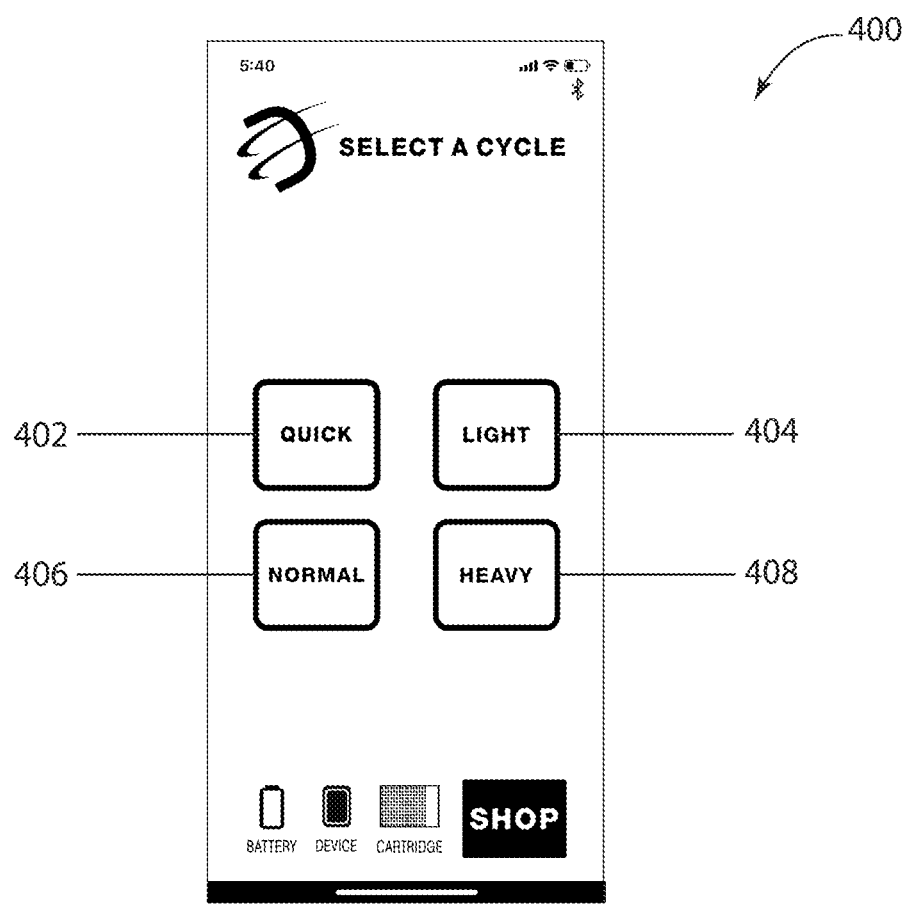
FIGS. 7A-7C shown embodiments of screenshots for mobile app used to control the ionic oxidation refreshing system and method.
Figure 7B:
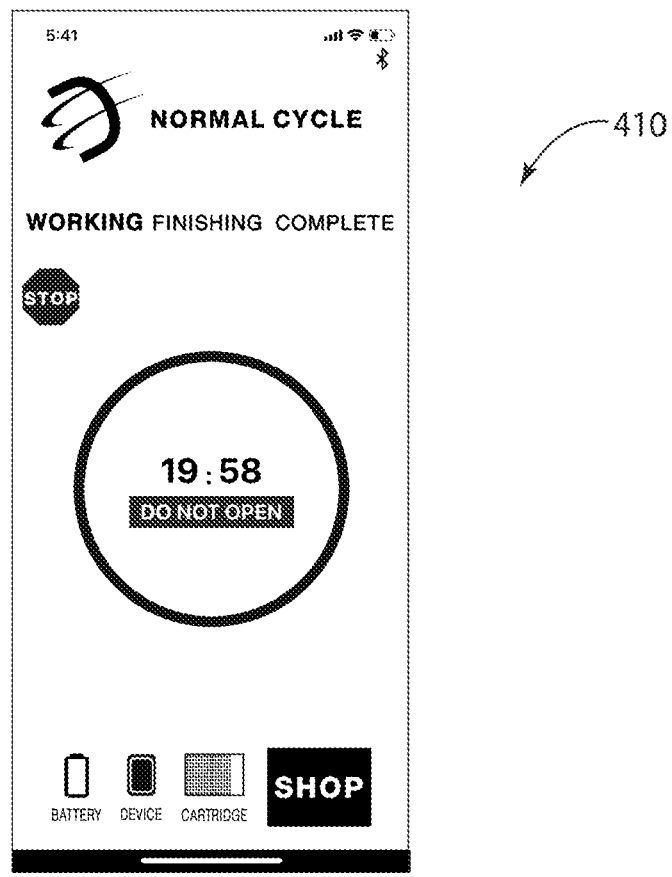
Figure 7C:
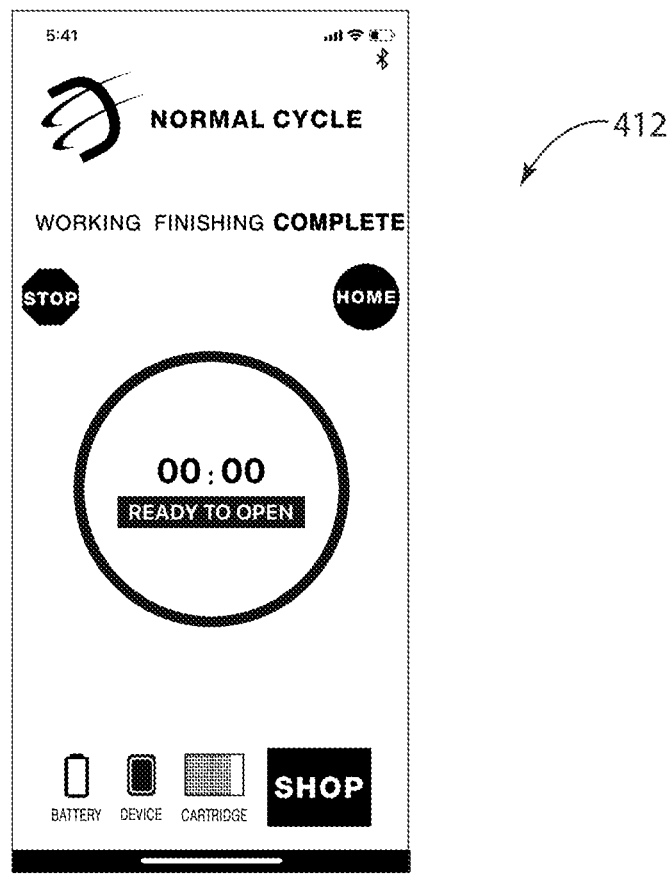

With reference to FIGS. 7A-C, in addition to controlling the module 120 via the RGB LED push button 310, the module 120 is configured to run using a smartphone app developed for both iOS and Android mobile computing devices. The user's smart device (e.g., smartphone, smartwatch, mobile computing device) wirelessly connects with the module 120 via a Bluetooth® connection. At screen 400, a user can select between a quick cycle 402, a light cycle 404, a normal cycle 406, and a heavy cycle 408. At screen 410, the selected cycle is displayed and information on the stages (e.g., working, finishing, complete) is displayed. Further, information on the time left in the cycle is displayed. At screen 412, the selected cycle is displayed and information on completion of the cycle is displayed. The screens 400, 410, 412 also display information on the module such as battery life, cartridge life and charging an external device. A shop function is also provided.

Figure 1E:
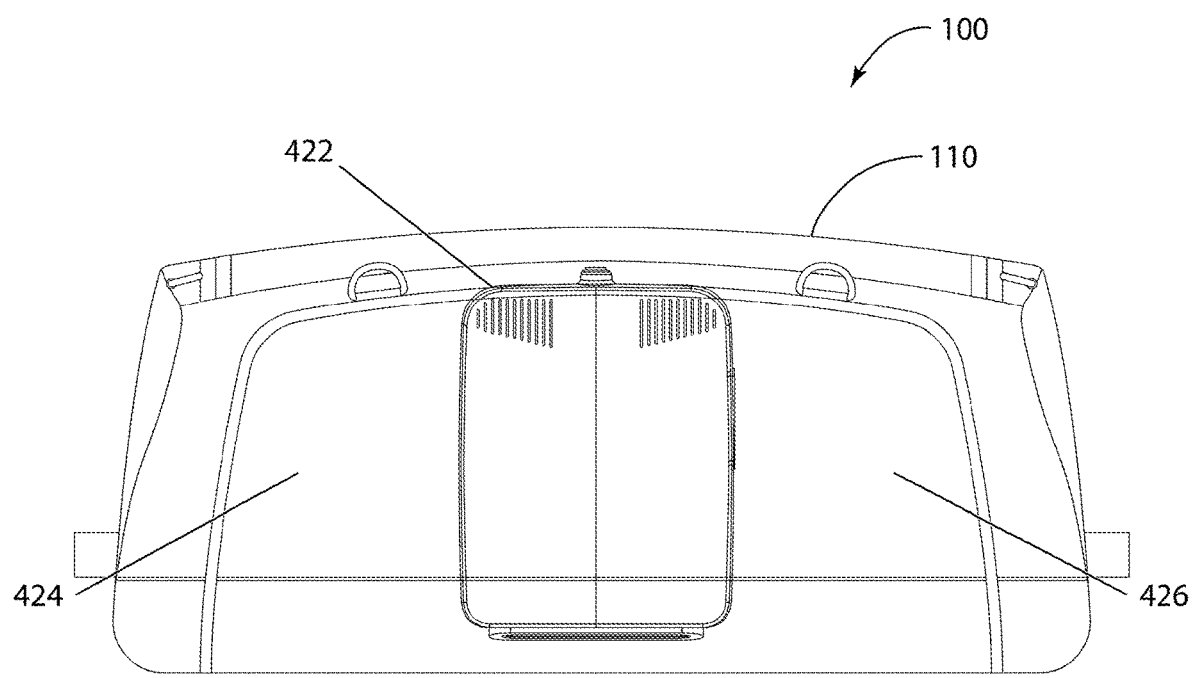
FIG. 1E is another rear side elevational view or pocket side view of the sports gym bag of FIG. 1A.
Figure 1F:
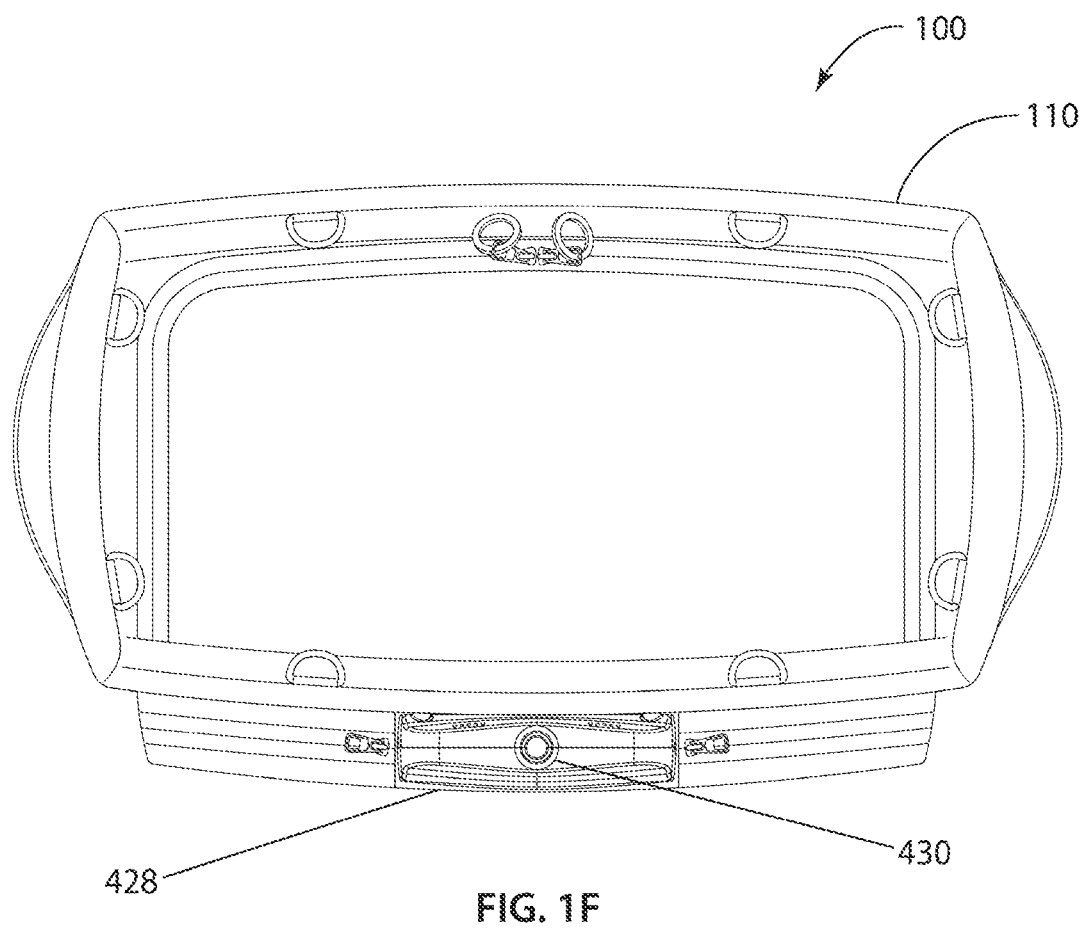
FIG. 1F is another top plan view or top view of the sports gym bag of FIG. 1A.
Figure 1G:
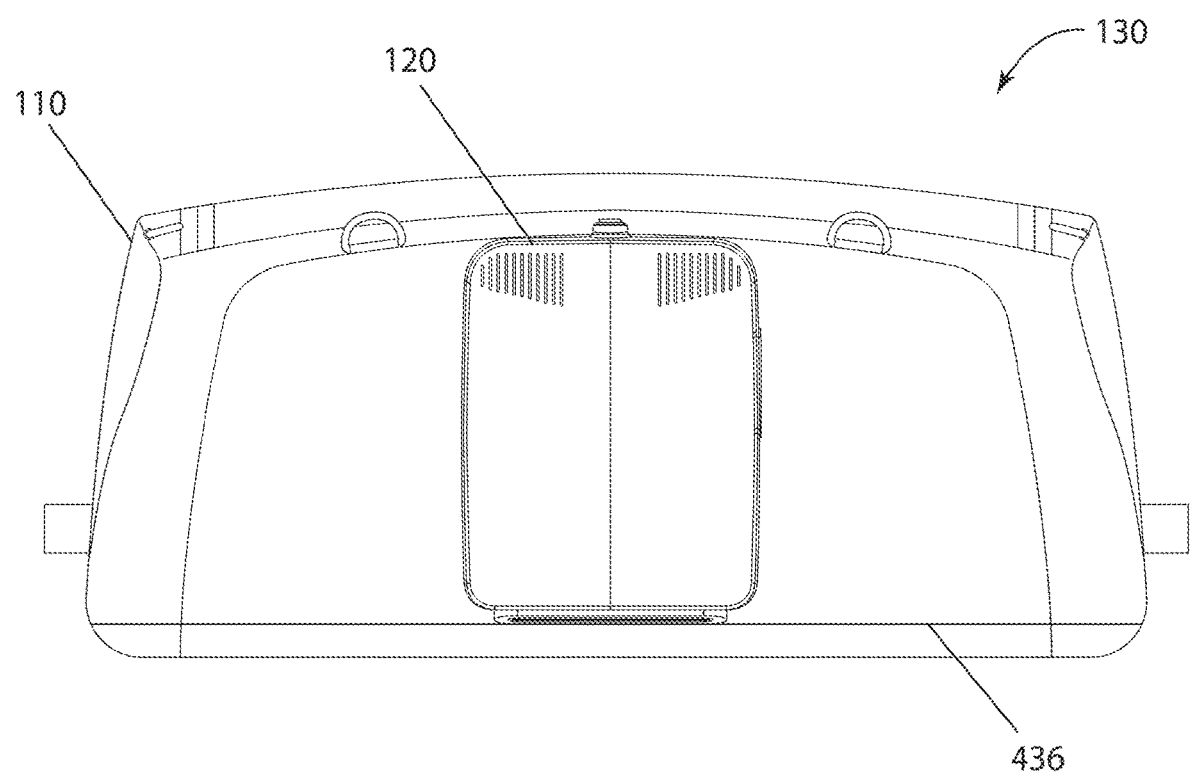
FIG. 1G is another rear side elevational view or pocket side view of the sports gym bag of FIG. 1A and shows an embodiment of a module for the sports gym bag.

With reference to FIGS. 1A-1F, FIGS. 4A-4B, FIGS. 5A-5B, and FIGS. 6A-6C, the sports gym bag 110 embodiment of the enclosure 130 will be described. The sports gym bag 110 includes a main clothing compartment 414 with a zip top 416, and a front pocket compartment 418 with zipper openings 420. As shown in FIGS. 1E and 1F, the front pocket compartment 418 includes a module pocket 422 to hold the module 120, a left external pocket 424 to access the hole or displaceable cartridge door 300 for inserting/removing the cartridge 170 into/from the cartridge slot/holder 220, and a right external pocket 426 for accessing USB and USB-C charger ports 270, 280. A top 428 of the module pocket 422 includes a trim ring 430 that receives the RGB LED push button 310.

Figures 4A, 4B:
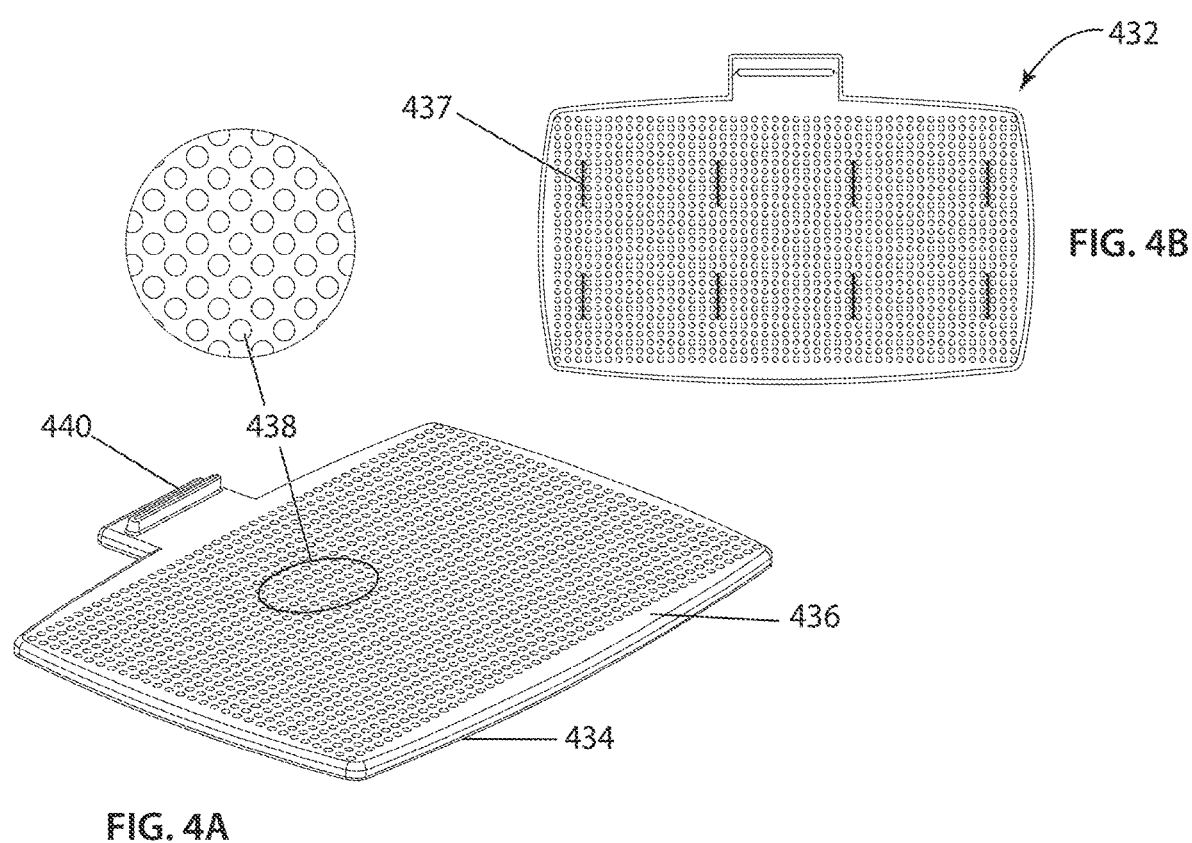
FIG. 4A is a top plan view of an embodiment of an airflow base and raised floor for the airflow system for the sports gym bag of FIGS. 1A-1F.
FIG. 4B is a front cross-sectional view of the airflow base and raised floor of FIG. 4A.
Figure 5A:
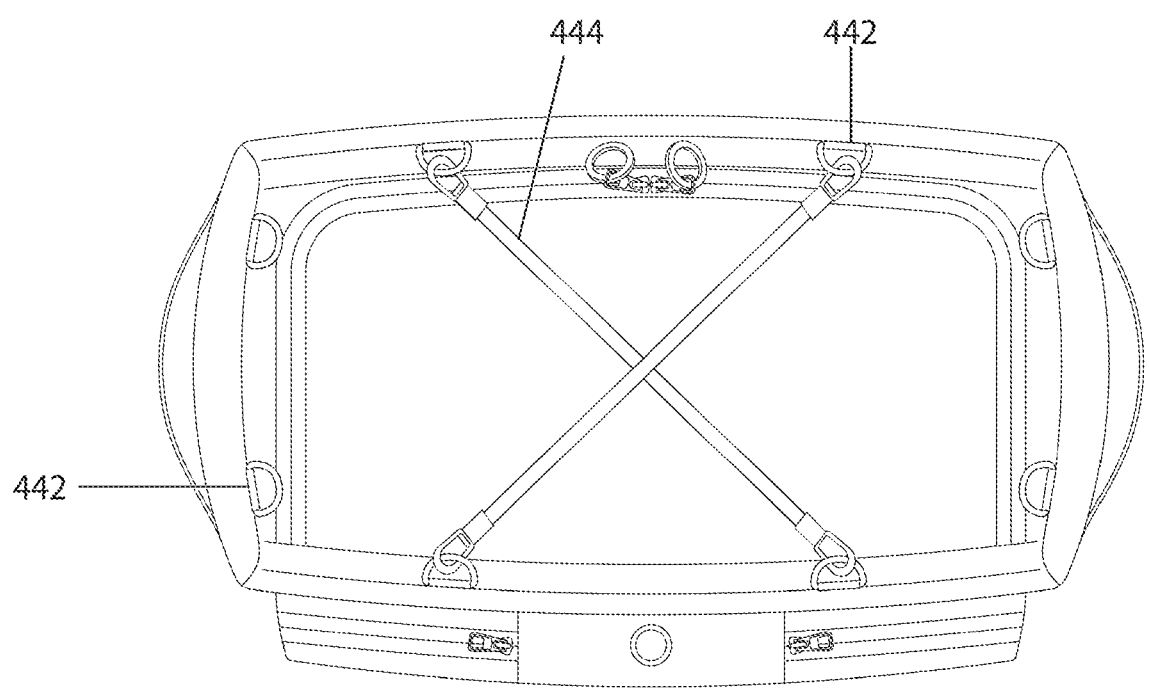
FIGS. 5A-5B show embodiments of bungee shock cord configurations for the sports gym bag of FIGS. 1A-1F.
Figure 5B:
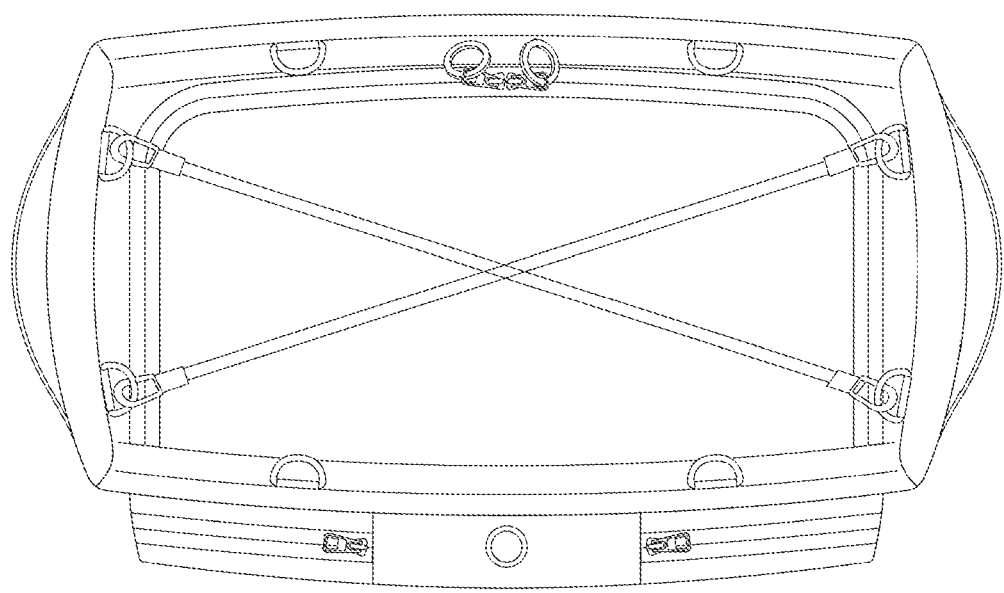
Figure 6A:
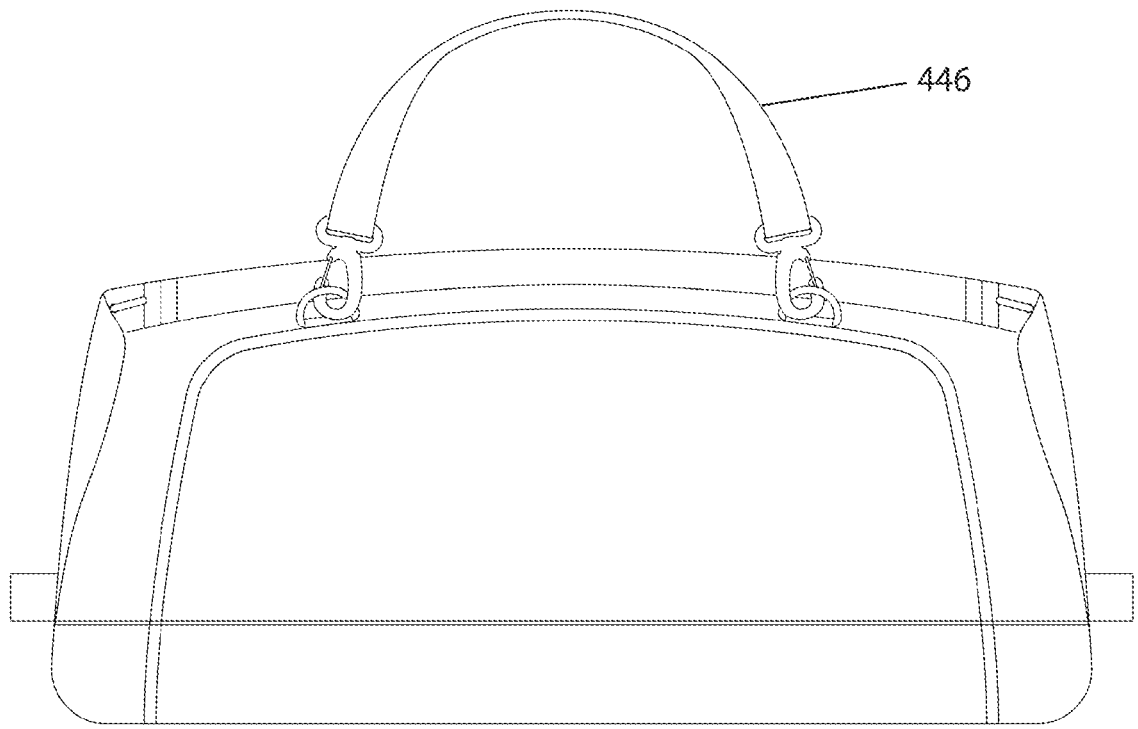
FIGS. 6A-6C show embodiments of handle/straps and/or configurations for the sports gym bag of FIGS. 1A-1F.
Figure 6B:
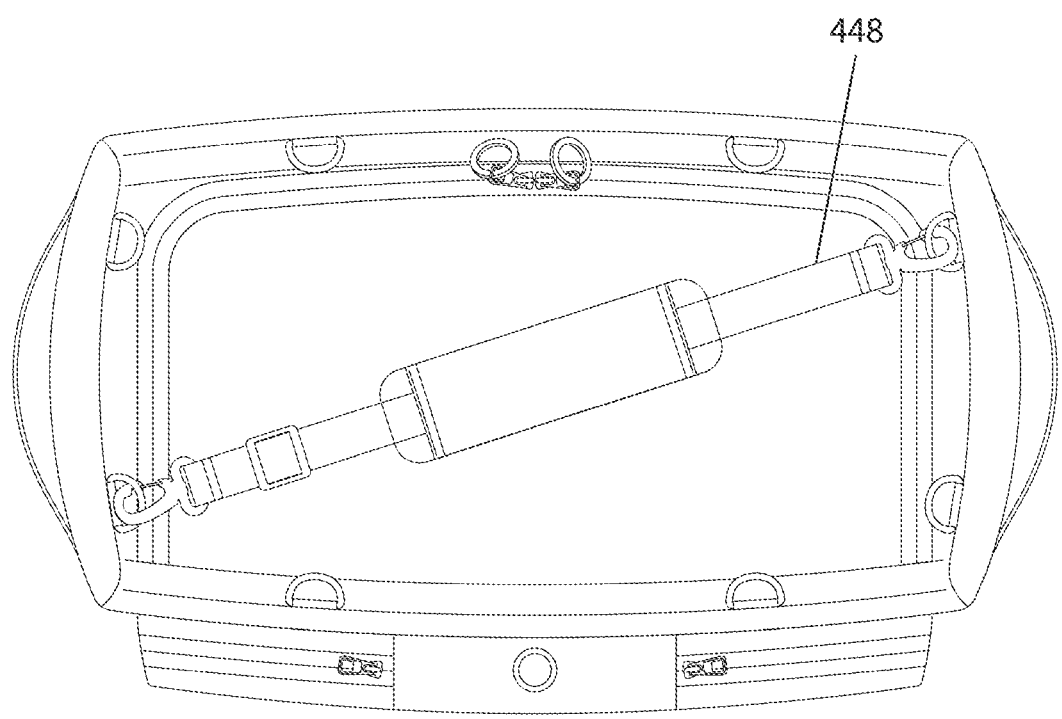
Figure 6C:
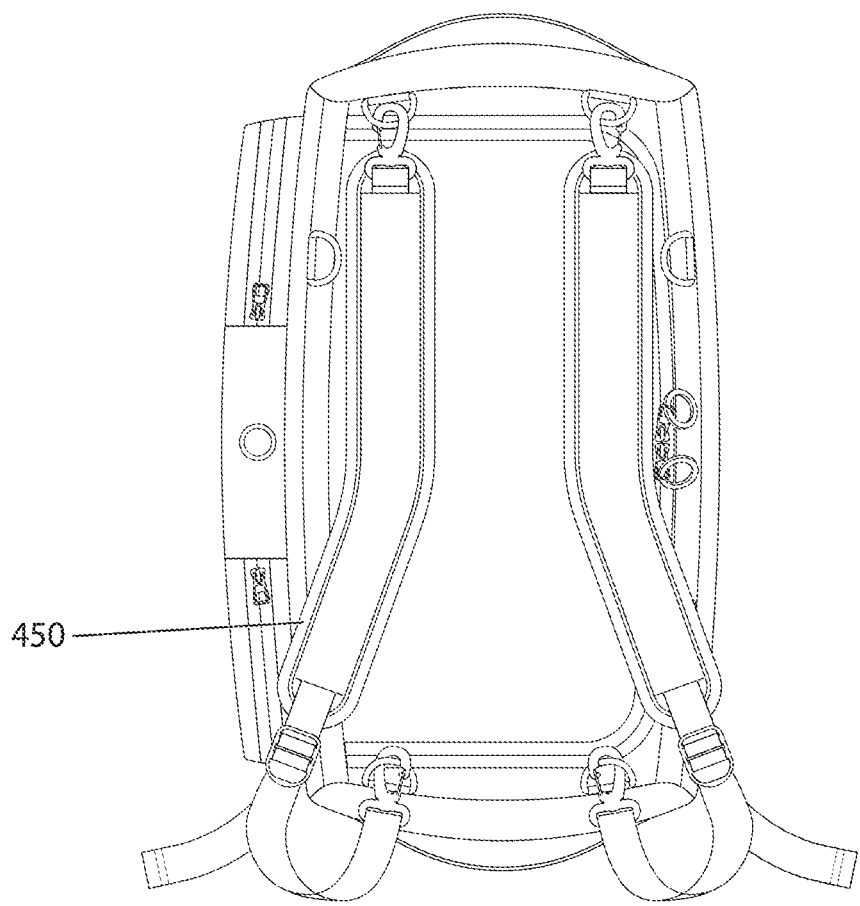

With reference to FIGS. 4A-4B, a bottom of the main clothing compartment 414 supports airflow base and raised floor assembly 432. The assembly 432 includes a bottom base 434 that rests on a bottom of the sports gym bag 110 and a raised floor grid 436 spaced upward from the bottom base 434 via a plurality of vertical supports 437. Round perforated holes 438 are disposed in the raised floor grid 436 and air outlet 440 is disposed on the top of raised floor grid 436 and between the vertical supports 437 to allow airflow through airflow system, which is made up of a main air moving/distribution mechanism (e.g., perforated grid base all as one piece placed in the bottom of the bag, or a perforated wall lining membrane in other enclosure designs), and the module with a guided output vent into the grid base or membrane lining.

With reference to FIGS. 5A-5B and FIGS. 6A-6C, the sports gym bag 110 may include a plurality of D-rings 442 strategically positioned to allow for the removable attachment of bungee cord(s) 444, carry handle(s) 446, shoulder strap 448, and backpack straps 450.

Some general features with respect to the enclosure 130 and the system as a whole will now be described. Proper materials must be used with the enclosure 130 to ensure resistivity to oxidation shock, and inertness to the process run inside. For example, a Teflon coating can be used on soft interior linings to protect them from oxidation. To help regulate internal humidity from damp items, a desiccant material may be used in the enclosure 130. This may be a separate desiccant filled pack, or an object made of a desiccant material, placed inside the enclosure 130 or the used items. Enclosure construction materials, such as the grid base or wall membrane, may be made of a desiccant material as well. This allows excess moisture to be absorbed by a desiccant material inside of the enclosure 130 as high relative humidity dampens the IOR process. A selectively permeable membrane can be used on external vents or side openings within the enclosure walls. This can help wet items placed inside dry by allowing water molecules, or excess moisture, to evaporate out. Maintaining optimal conditions for the IOR process inside helps deliver more consistent results and a better user experience. This is done by ensuring the enclosure 130 is air-tight and has minimal leaks. Seals are used in any areas that open, to keep the gas from escaping during operation. This is important, as the preset IOR cycles are developed to reach specific gas concentrations within the enclosure 130 to ensure effective deodorizing and sanitizing of items inside.

Various enclosure designs including, but not limited to, duffel bags, backpacks, suitcases, plastic bins, locker units, garment bags, closet systems, laundry hampers, and stand-alone appliances give way to different configurations of the hardware. Consequently, the module 120 may be powered by the rechargeable battery 200 or wall outlet. This allows for portable and stationary versions of the ionic oxidation refreshing system 100 and method. Different design requirements of each form factor lead to a wide variety of airflow system designs to ensure consistent process results.

As shown and described with respect to FIGS. 4A-4B, an open-air grid can be used in the base or walls for some designs, whereas a perforated air membrane must be used for others. This depends on the orientation and shape of the enclosure housing.

As shown and described with respect to FIGS. 3A-3B and FIGS. 7A-7C, a user can select which cycle to run using one's smart device (e.g., smartphone, smartwatch, mobile computing device). An app connects to the module via Bluetooth® or Wi-Fi to allow for convenient control. It also gives notifications to the user about battery level, cartridge level and cycle status. The module features a color changing push button that displays different colors depending on the cycle stage or notification given. This push button is easily visible on the enclosure 130, allowing users to clearly see cycle progress and quickly stop a cycle during operation if needed. Other models, such as stand-alone appliances, may feature a large touchscreen display instead of an app interface The filter cartridge 170 may have a cartridge solution including the following: gel or liquid formula with process by-product scrubbing compounds which may include: a blend of metal nanoparticle solutions; manganese oxide solutions, salt solutions; sodium bicarbonate solutions; hydroxides or peroxides; silicon dioxides; and natural essential oils and/or synthetic fragrance oils. The cartridge 170 ensures a consistent user experience by scrubbing out leftover gases and ions; and eliminates oxidation by-products such as VOCs or aldehydes created from the rapid oxidation of items, or ozone and nitric acids created from the ionization of air. The creation of nitric acid occurs because of the presence of water moisture and nitrogen in ambient air. This can leave behind a pungent odor if not neutralized with a basic scrubbing compound of higher pH, such as sodium bicarbonate, in the filter formula. Eliminating these by-products leads to a safer and enhanced user experience, and boosts process performance. The natural essential oils and/or synthetic fragrance oils release scent molecules capable of adhering to items inside of the enclosure 130, in order to release a stronger therapeutic aroma over time. These scent molecules are charged negatively by the anion diffuser, opposite to the items being refreshed inside, which are charged more positively on their surfaces by the ionized airflow in the first process stage. This allows them to attract and stick to the surfaces of these refreshed items inside more easily. This allows the items to keep a fresh aroma for a longer period. Activated carbon may be used as a pre-filter, separate from the cartridge 170, or included as a lining/layer on top of the cartridge 170 to capture pollutants, such as certain VOCs, not eliminated by the process filtering stage.

Figure 8:
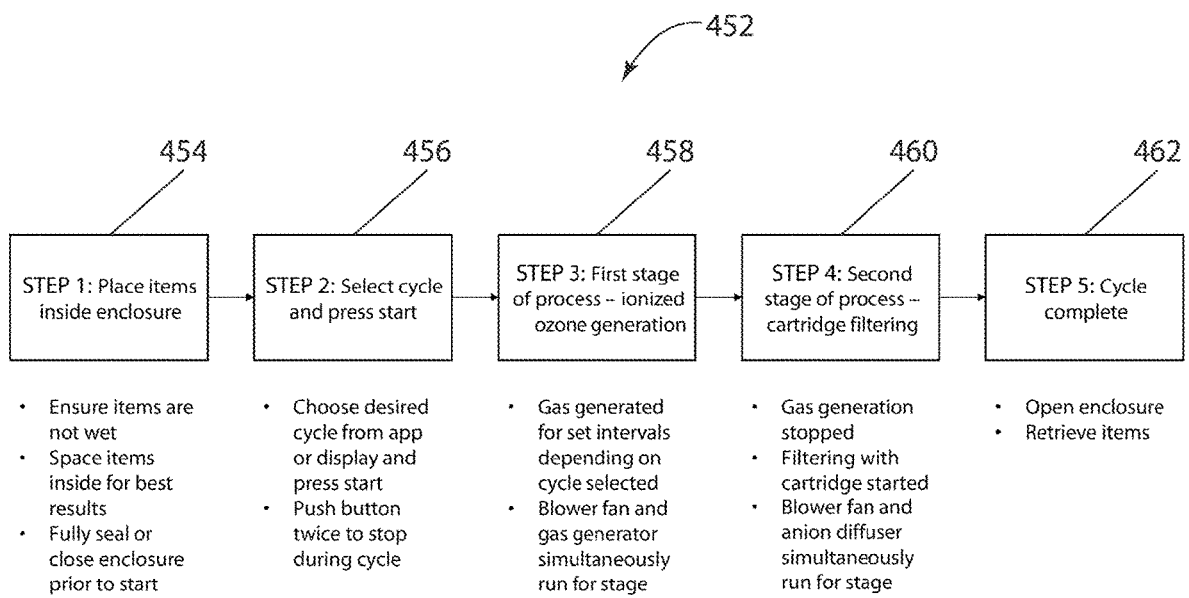
FIG. 8 is an exemplary flow chart of the ionic oxidation refreshing method.

With reference to FIG. 8, an exemplary flow chart of an ionic oxidation refreshing method ("IOR process") 452 will be described. The IOR process 452 is designed to kill germs and eliminate odors on items being refreshed inside of the enclosure 130. At step 1 (454), items are placed inside the enclosure 130. It is important to ensure items are not wet, items are spaced inside for best performance, and that the enclosure 130, and any pockets or openings, are fully sealed prior to start. At step 2 (456), the appropriate cycle is selected and started. A person can select one of four cycles from the phone app that connects with the module. The cycle picked depends on the odor level and number of items being refreshed. Each cycle has preprogrammed stage times and run automatically once started. Staggered generation times are used to maintain optimal element operating characteristics. This helps ensure precise element temperature and protects it from short circuiting due to high cation electric flux density on the element surface. The desired cycle is chosen from the app (or a display) and start is pressed. The use of software with an item database can allow the user to select what has been placed inside of the enclosure 130. This allows for the creation of custom cycle runs by adjusting process parameters based on the selected items. Sensory inputs may also be employed to create fully autonomous cycle runs, adjusted to the items inside, and live process input parameters. A VOC sensor 140 can be used as an input to the process. This allows for live measurement of odor levels from items inside before and during the process run. The use of a relative humidity (RH) and temperature sensor 140 can provide process input to help monitor enclosure conditions and adjust generating times for maintaining optimal gas concentrations for better cleaning performance. There is an inverse relationship between gas generation and the relative humidity (RH) of the enclosure 130. An ozone sensor 140 can also be used to control process generation precisely instead of pre-determined time intervals. However, this is not currently an economical option to use for consumer products due to the cost and size of these sensors. The use of a specifically designed air sensor 140 that measures RH, temperature, VOCs, and particle count, such as ions, inside of the enclosure 130 can be used instead. This sensor can provide live process inputs at an economical cost to enhance process performance inside of any enclosure. A smart setting is used to adjust process stages from sensory inputs in real time, during a cycle run. At step 3 (458), the first stage of the process, ionized gas generation occurs. At this stage, gas is generated for fixed time intervals depending on the cycle selected, and a circulation fan and corona discharge gas generator are simultaneously run. Air inside the enclosure 130 is ionized using the corona discharge element/device 160, which may comprise of ceramic, stainless steel, or quartz glass elements in a plate, disc, cylinder, wire, or a configuration of shapes, to generate the supercharged gas. This element may also be a hybrid, such as a ceramic coated with a ruthenium and metal paste glass glaze finish, to maximize generation. This also increases component life, by preventing build-up of oxidized pollutants found in air on the element, which can short-circuit the element and hamper generation. Gas is produced at a rate ranging from 10 mg/hr to 1000 mg/hr depending on the enclosure design requirements. This supercharged gas reaches concentrations between 1 ppm and 100 ppm inside of the enclosure 130, depending on the number of items placed inside and the cleaning cycle selected. A catalyst device 142 may be used to boost process performance. Ultraviolet light emitting diodes in the c-spectrum (UV-C LEDs), may be used to partially ionize incoming charged gas to module 120 from the filtering stage. The light should be predominately in the c-spectrum for it to be effective for breaking down generated gases from the first stage. It is not effective to use UV-C LEDs inside of an enclosure 130 during a generating stage, as they will have an adverse effect on overall gas concentration. An ultrasonic transducer can be used in the device for agitating gases inside by high frequency vibrations. This will increase the rate of particle collisions inside of the enclosure 130, speeding up the IOR process. The ionized ozone is circulated inside by means of the fan 190 and the specially designed airflow system 150 within the enclosure 130. This supercharged airflow kills microorganisms it encounters on the surface of items, effectively eliminating any odors as well. By killing most germs and odors on an item, it feels refreshed to the person and comfortable to use again. At step 4 (460), the second stage of the process, cartridge filtering occurs. At this stage, gas generation is stopped, the anion diffuser now runs with the circulation fan, and filtering with the cartridge is performed until the cycle time is completed. An anion diffuser 180 is used to accelerate the filtering process. A high electric flux density of negative ions neutralizes any remaining highly charged positive ions and charges outgoing scent molecules. The IOR process works like an ion exchange system during the first stage to the second stage to scrub out process by-product compounds using the gel polymer filter 170. This cartridge filtering stage ensures process safety, optimal cleaning performance, and an enhanced user experience. The cartridge 170 filters out any toxic gases or compounds, such as ozone and nitric acid, at the end of a generating stage. It also scrubs out process by-products, such as VOCs or aldehydes, and releases a fresh scent into the enclosure 130 as it reacts away any remaining ionized ozone gas. At step 5 (462), the cycle is complete. At this stage, the user opens the enclosure/bag 130 to a nice aroma and retrieves their items, refreshed and ready to use again. The IOR process uses the combination of ionized ozone and the quick cleaning filter cartridge 170 to deliver more consistent results across a multitude of items. This is accomplished by using the supercharged gaseous mixture to react with an oxidizing catalyst that increases the concentration of radical ions and in turn, the cleaning performance of the process. The catalyst, which is a separate consumable piece near the generating element and/or a oxidized coating on the generating element, is used to increase concentrations of cations and free radicals created in the first stage. This may be a metal such as copper, nickel, aluminum or other metals which have a net positive charge and release cations by oxidization. The increase of these powerful oxidizers increases the oxidizing power of any ozone gas created as well, and in turn, supercharges, or potentiates, the overall gas mixture with ozone to a higher oxidative power. The unique mix of this gas allows it to clean better and faster than ozone gas alone. It also reduces the number of toxic compounds, such as aldehydes or VOCs, that may be released into the enclosure 130 from the rapid oxidation of items inside through high energy interactions. The ionized ozone gas is then reacted with a cartridge formula for filtering, or scrubbing, these by-products out. These scrubbing compounds eliminate any gases and toxic compounds released into the enclosure 130 from the generating stage and rapid oxidation of items. A filtering device, such as an anion generator, is used in the finishing stage to improve the scrubbing process by neutralizing remaining cations. It also charges scent molecules being released from the filter cartridge. These molecules obtain a net negative charge, opposite to the surface of items inside holding a net positive charge. This allows the scent molecules to adhere to items being refreshed inside more easily. Steam may be used during or after the filtering stage to remove wrinkles on dress clothing placed inside other enclosure designs, such as closets or stand-alone appliances. These systems require a direct line water supply and high-pressure boiler to inject hot steam inside.

Figure 9:
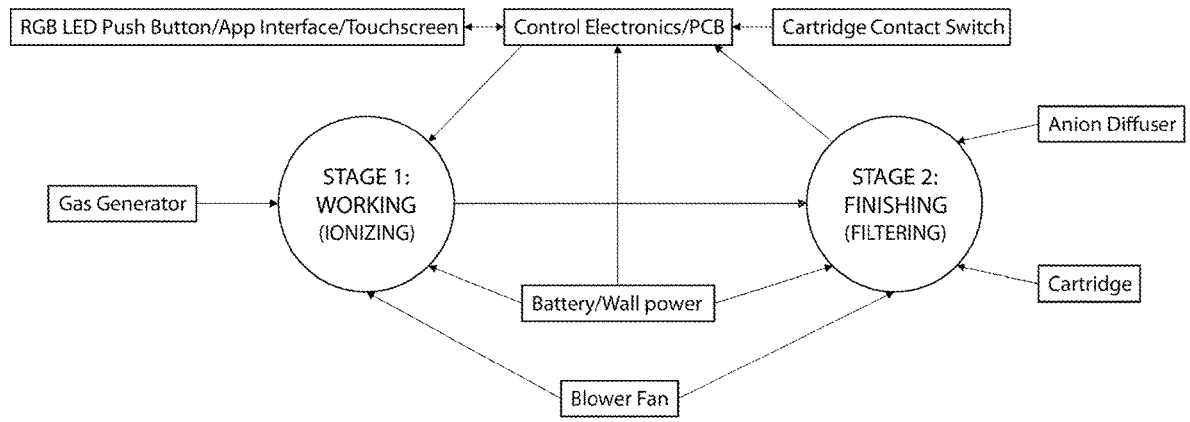
FIG. 9 is an exemplary component block diagram of the ionic oxidation refreshing method.

FIG. 9 is an exemplary component block diagram of the ionic oxidation refreshing method, and illustrates the components of the system involved in the first stage of the process, ionized ozone gas generation, namely, RGB LED push button, PCB/electronics, rechargeable battery, blower fan, corona discharge generator, and cartridge contact switch, and the components of the system involved in the second stage of the process, cartridge filtering, namely, RGB LED push button, PCB/electronics, rechargeable battery, blower fan, anion diffuser, cartridge, and cartridge contact switch.

The ionic oxidation refreshing system 100 and method gives consumers the ability to inexpensively and conveniently micro-clean items such as clothing and sports gear after use. Since most items are usually not very dirty after one wear or use, they can maintain items between uses. This effectively reduces the time and resources required by excessive cleaning and extends an item's usable life. These new IOR process appliances will give an economical alternative solution to traditional cleaning methods used today. The impact of excessive laundering, dry-cleaning, and chemical use by individual households will be minimized, along with their environmental impact. Current consumer solutions are incomplete as they do not deliver consistent results on many items like the IOR process can. A better appliance is needed for the consumer market that can deliver an enhanced user experience. Market research has shown people's experiences with other products are unsatisfactory as most people relate cleanliness to a fresh scent on an item primarily, if no other dirt, grime, or stains are visible. Current solutions to the outlined problems do not offer this experience and thus have fallen short on customer expectations. Systems or appliances relying on ozone gas alone are not capable of delivering strong and consistent results due to the high concentrations of the gas they use and process by-products that are not eliminated. Only the IOR process uses a novel combination of cleaning agents, along with a cartridge containing formula that scrubs out remaining gases and process by-products, while leaving behind a fresh scent. The user opens the enclosure 130 to an aroma inside that smells pleasant and gives the user a psychological trigger that the items inside have been cleaned. Commercial advantages of the ionic oxidation refreshing system 100 and method include, but are not limited to, building the IOR process into various enclosure designs such as portable bags and bins, or stand-alone appliances; saves time and money on utilities, cleaning supplies, and professional services; and allows user to re-wear previously worn items without excessive cleaning. Technological advantages of the ionic oxidation refreshing system 100 and method include, but are not limited to, using a light refreshing process extends items life compared with other methods, requires minimal power to run, is more convenient to use often, and micro-cleaning is an economical and green alternative.

System Overview

Infrastructure

Figure 10:
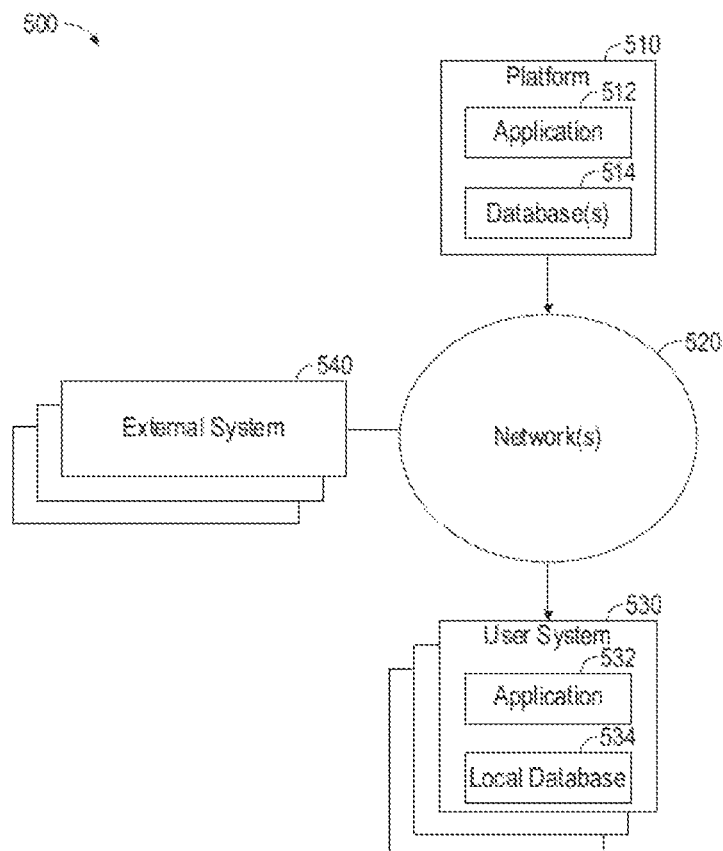
FIG. 10 illustrates an example infrastructure, in which one or more of the processes described herein, may be implemented, according to an embodiment.

FIG. 10 illustrates an example system 500 that may be used, for example, but not by way of limitation, for controlling the ionic oxidation refreshing method through the smart phone app, according to an embodiment. The infrastructure may comprise a platform 510 (e.g., one or more servers) which hosts and/or executes one or more of the various functions, processes, methods, and/or software modules described herein. Platform 510 may comprise dedicated servers, or may instead comprise cloud instances, which utilize shared resources of one or more servers. These servers or cloud instances may be collocated and/or geographically distributed. Platform 510 may also comprise or be communicatively connected to a server application 512 and/or one or more databases 514. In addition, platform 510 may be communicatively connected to one or more user systems 530 via one or more networks 520. Platform 510 may also be communicatively connected to one or more external systems 540 (e.g., other platforms, websites, etc.) via one or more networks 520.

Network(s) 520 may comprise the Internet, and platform 510 may communicate with user system(s) 530 through the Internet using standard transmission protocols, such as HyperText Transfer Protocol (HTTP), HTTP Secure (HTTPS), File Transfer Protocol (FTP), FTP Secure (FTPS), Secure Shell FTP (SFTP), and the like, as well as proprietary protocols. While platform 510 is illustrated as being connected to various systems through a single set of network(s) 520, it should be understood that platform 510 may be connected to the various systems via different sets of one or more networks. For example, platform 510 may be connected to a subset of user systems 530 and/or external systems 540 via the Internet, but may be connected to one or more other user systems 530 and/or external systems 540 via an intranet. Furthermore, while only a few user systems 130 and external systems 540, one server application 512, and one set of database(s) 514 are illustrated, it should be understood that the infrastructure may comprise any number of user systems, external systems, server applications, and databases.

User system(s) 530 may comprise any type or types of computing devices capable of wired and/or wireless communication, including without limitation, desktop computers, laptop computers, tablet computers, smart phones or other mobile phones, servers, game consoles, televisions, set-top boxes, electronic kiosks, point-of-sale terminals, Automated Teller Machines, and/or the like.

Platform 510 may comprise web servers which host one or more websites and/or web services. In embodiments in which a website is provided, the website may comprise a graphical user interface, including, for example, one or more screens (e.g., webpages) generated in HyperText Markup Language (HTML) or other language. Platform 510 transmits or serves one or more screens of the graphical user interface in response to requests from user system(s) 530. In some embodiments, these screens may be served in the form of a wizard, in which case two or more screens may be served in a sequential manner, and one or more of the sequential screens may depend on an interaction of the user or user system 530 with one or more preceding screens. The requests to platform 510 and the responses from platform 510, including the screens of the graphical user interface, may both be communicated through network(s) 520, which may include the Internet, using standard communication protocols (e.g., HTTP, HTTPS, etc.). These screens (e.g., webpages) may comprise a combination of content and elements, such as text, images, videos, animations, references (e.g., hyperlinks), frames, inputs (e.g., textboxes, text areas, checkboxes, radio buttons, drop-down menus, buttons, forms, etc.), scripts (e.g., JavaScript), and the like, including elements comprising or derived from data stored in one or more databases (e.g., database(s) 514) that are locally and/or remotely accessible to platform 510. Platform 510 may also respond to other requests from user system(s) 530.

Platform 510 may further comprise, be communicatively coupled with, or otherwise have access to one or more database(s) 514. For example, platform 510 may comprise one or more database servers which manage one or more databases 514. A user system 530 or server application 512 executing on platform 510 may submit data (e.g., user data, form data, etc.) to be stored in database(s) 514, and/or request access to data stored in database(s) 514. Any suitable database may be utilized, including without limitation MySQL™ Oracle™, IBM™, Microsoft SQL™, Access™, and the like, including cloud-based databases and proprietary databases. Data may be sent to platform 510, for instance, using the well-known POST request supported by HTTP, via FTP, and/or the like. This data, as well as other requests, may be handled, for example, by server-side web technology, such as a servlet or other software module (e.g., comprised in server application 512), executed by platform 510.

In embodiments in which a web service is provided, platform 510 may receive requests from external system(s) 540 and provide responses in extensible Markup Language (XML), JavaScript Object Notation (JSON), and/or any other suitable or desired format. In such embodiments, platform 510 may provide an application programming interface (API) which defines the manner in which user system(s) 530 and/or external system(s) 540 may interact with the web service. Thus, user system(s) 530 and/or external system(s) 540 (which may themselves be servers), can define their own user interfaces, and rely on the web service to implement or otherwise provide the backend processes, methods, functionality, storage, and/or the like, described herein. For example, in such an embodiment, a client application 532 executing on one or more user system(s) 530 may interact with a server application 512 executing on platform 510 to execute one or more or a portion of one or more of the various functions, processes, methods, and/or software modules described herein. Client application 532 may be "thin," in which case processing is primarily carried out server-side by server application 512 on platform 510. A basic example of a thin client application is a browser application, which simply requests, receives, and renders webpages at user system(s) 530, while the server application on platform 510 is responsible for generating the webpages and managing database functions. Alternatively, the client application may be "thick," in which case processing is primarily carried out client-side by user system(s) 530. It should be understood that client application 532 may perform an amount of processing, relative to server application 512 on platform 510, at any point along this spectrum between "thin" and "thick," depending on the design goals of the particular implementation. In any case, the application described herein, which may wholly reside on either platform 510 (e.g., in which case server application 512 performs all processing) or user system(s) 530 (e.g., in which case client application 532 performs all processing) or be distributed between platform 510 and user system(s) 530 (e.g., in which case server application 512 and client application 532 both perform processing), can comprise one or more executable software modules that implement one or more of the functions, processes, or methods of the application described herein.

Example Processing Device

Figure 11:
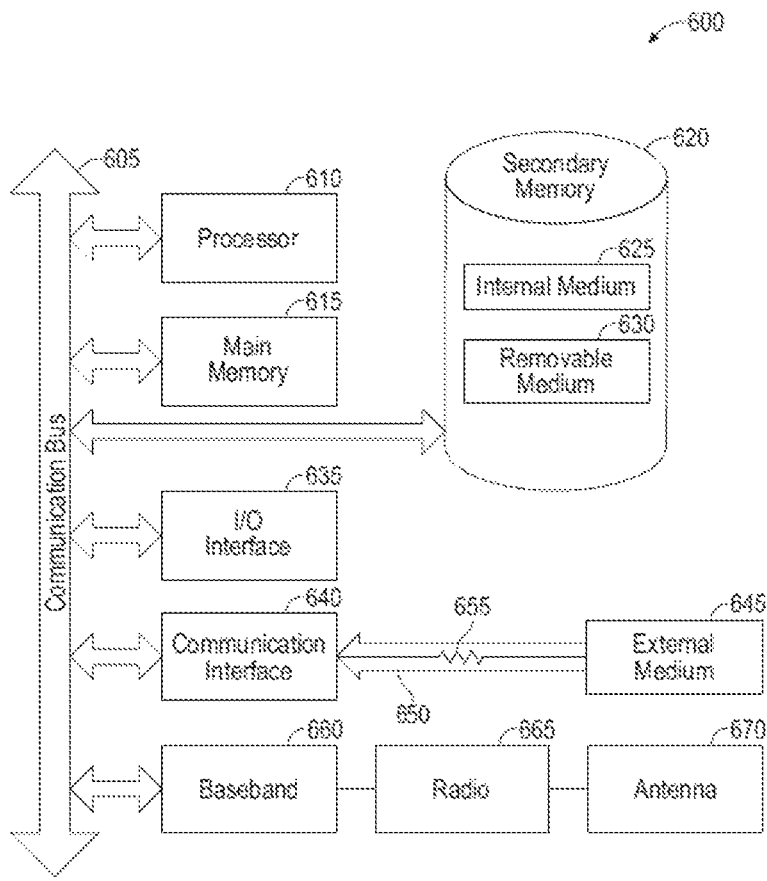
FIG. 11 illustrates an example processing system, by which one or more of the processed described herein, may be executed, according to an embodiment.
Figure 12:
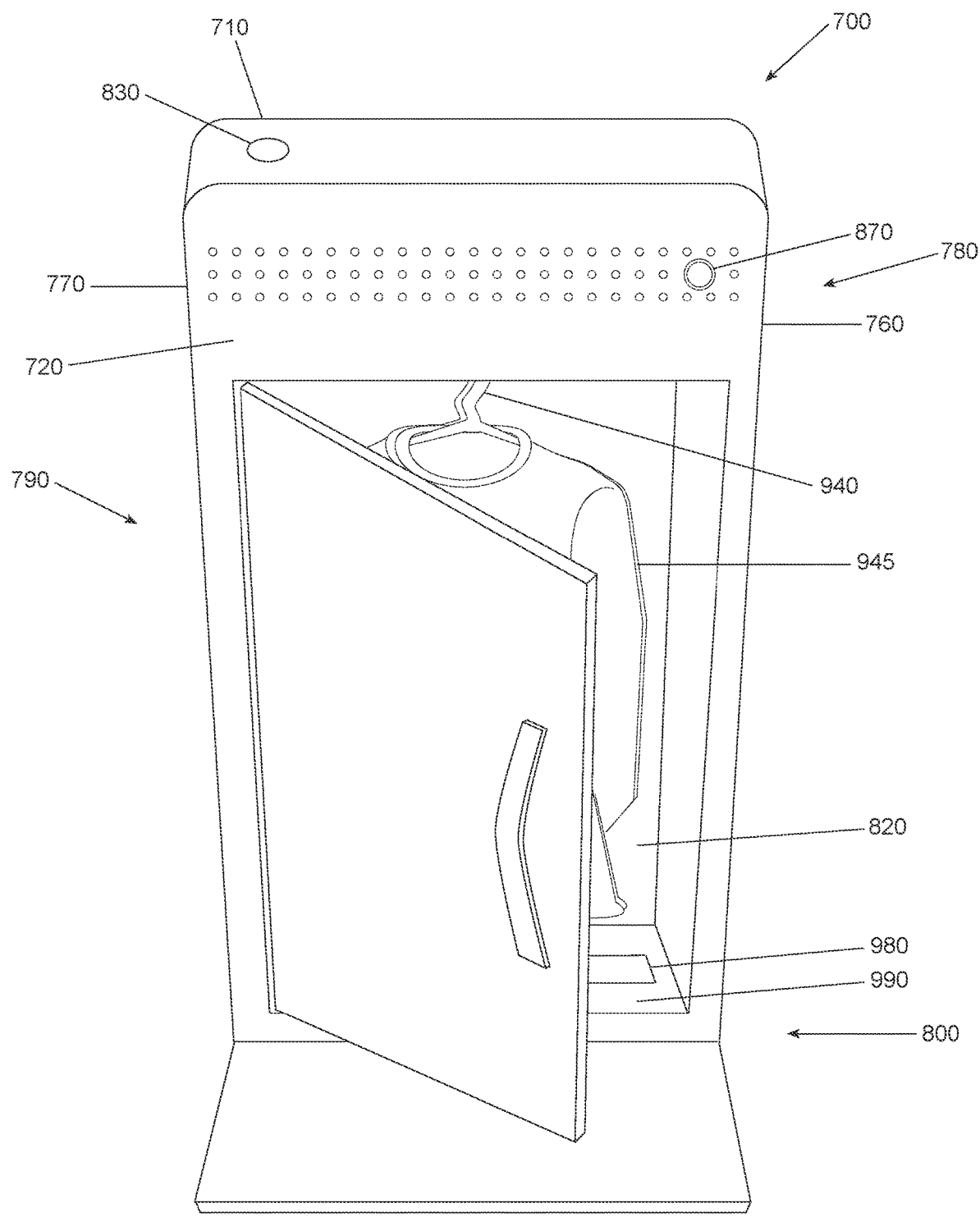
FIG. 12 is a front perspective view of an another embodiment of an ionic oxidation refreshing system.
Figure 13:
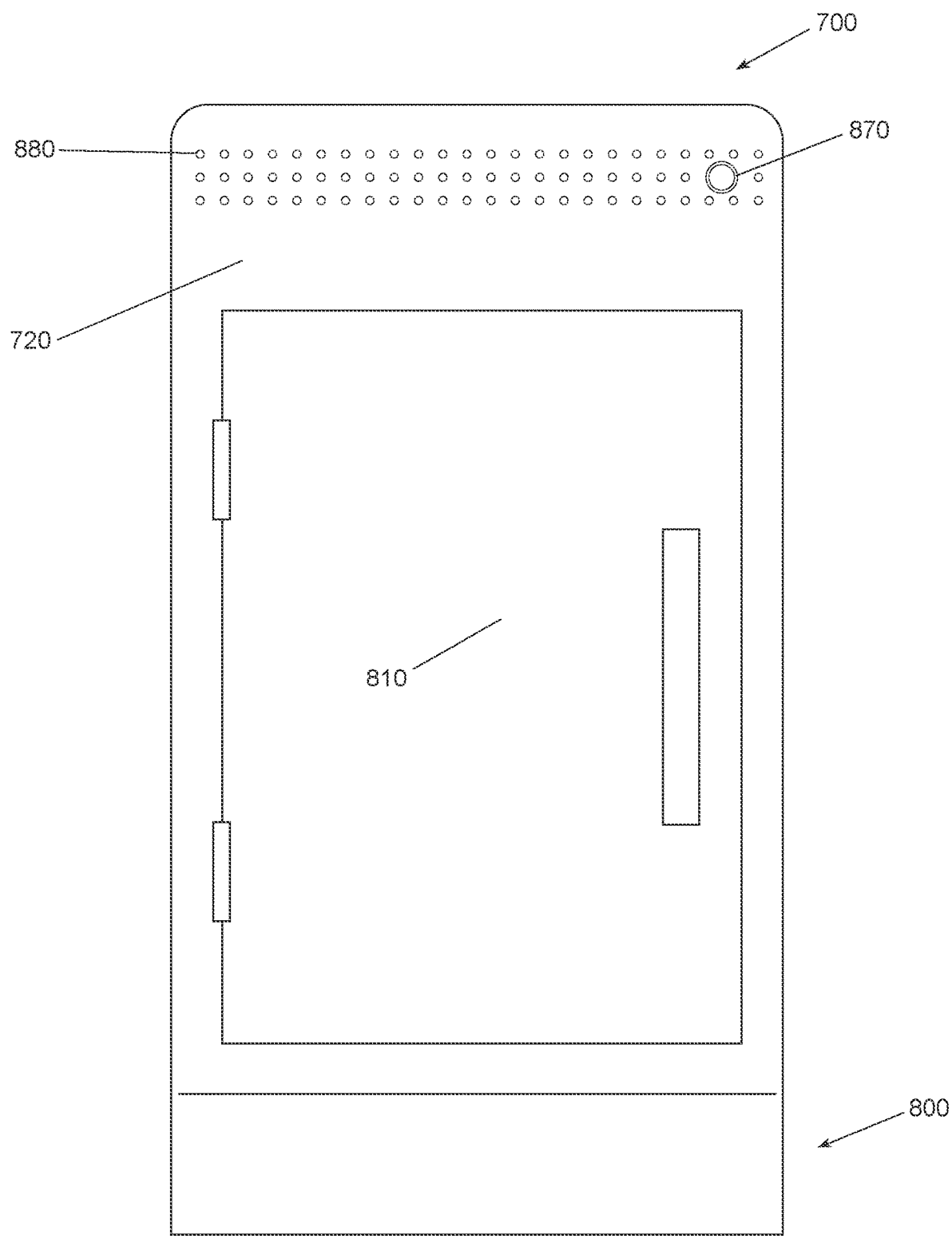
FIG. 13 is a front elevational view of the ionic oxidation refreshing system of FIG. 12.
Figure 14:
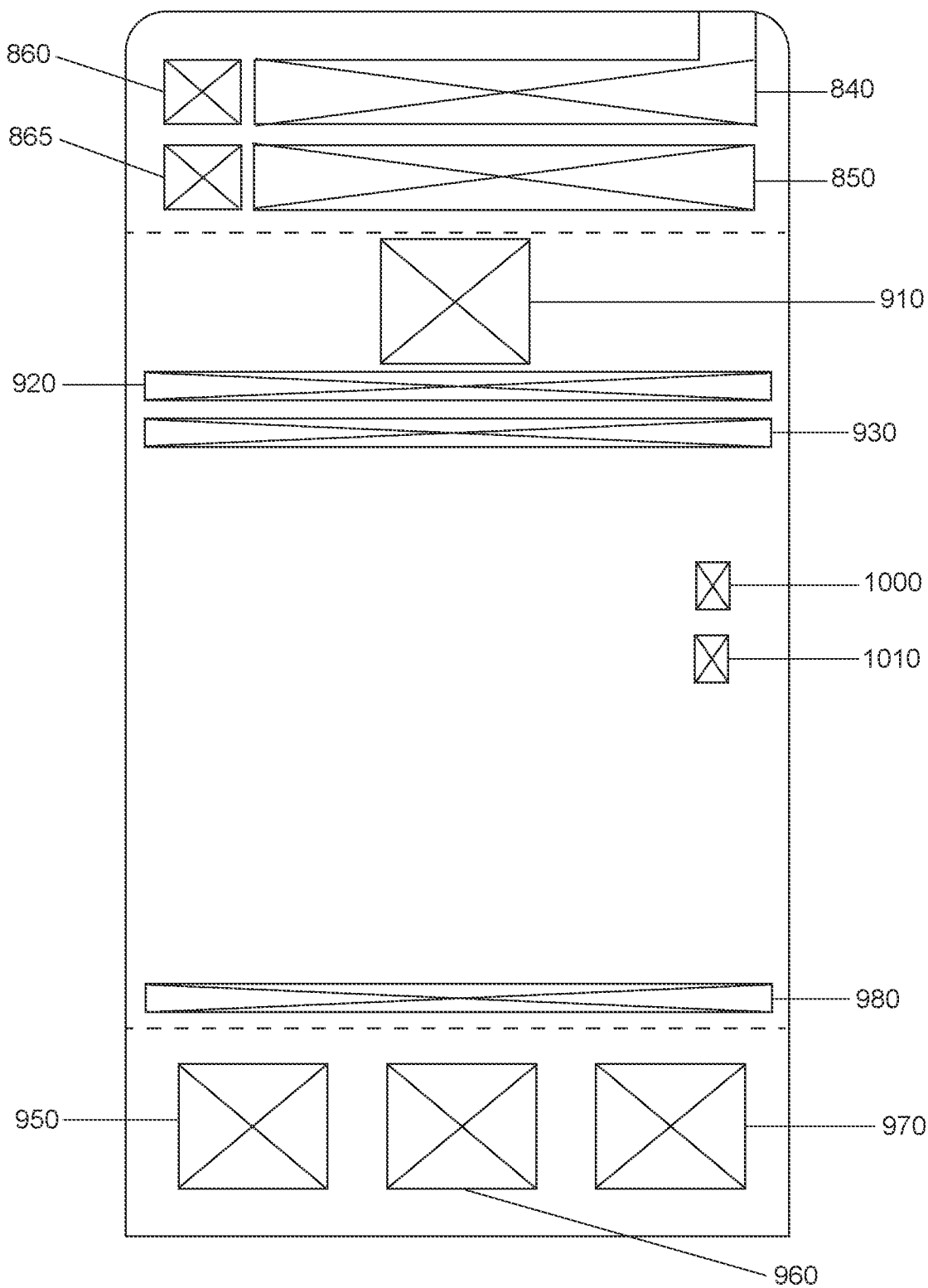
FIG. 14 is a schematic of the ionic oxidation refreshing system of FIG. 12.
Figure 15:
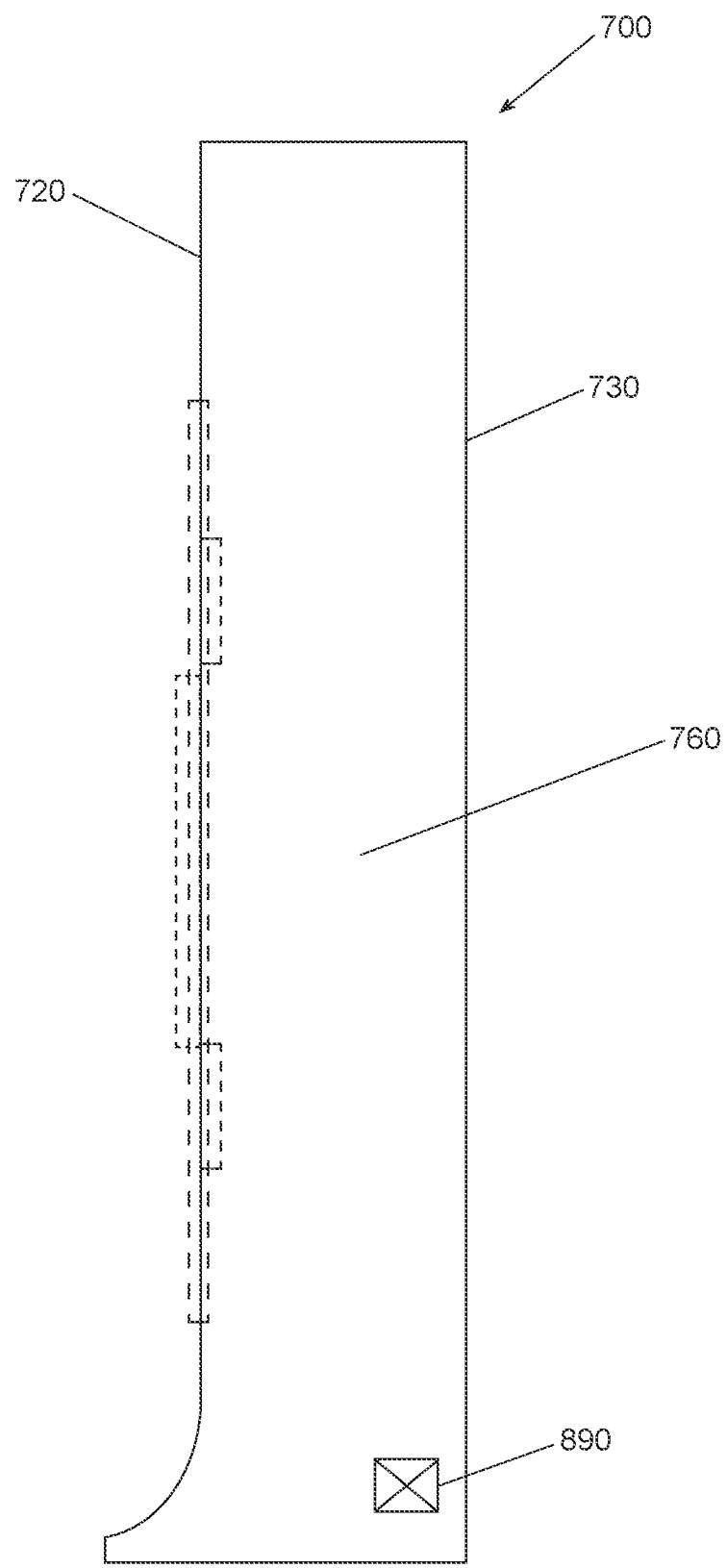
FIG. 15 is a right side elevational view of the ionic oxidation refreshing system of FIG. 12.
Figure 16:
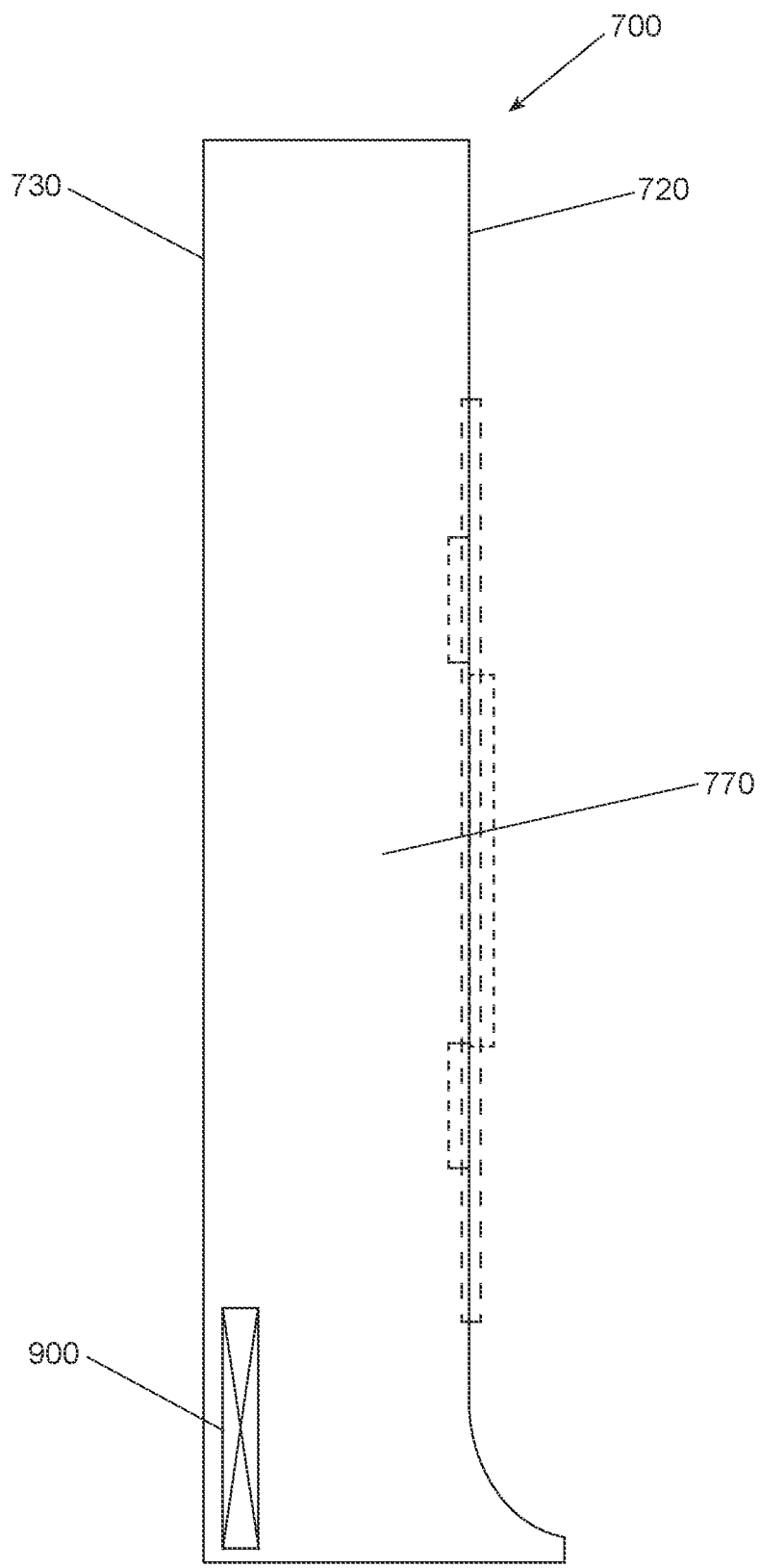
FIG. 16 is a left side elevational view of the ionic oxidation refreshing system of FIG. 12.
Figure 17:
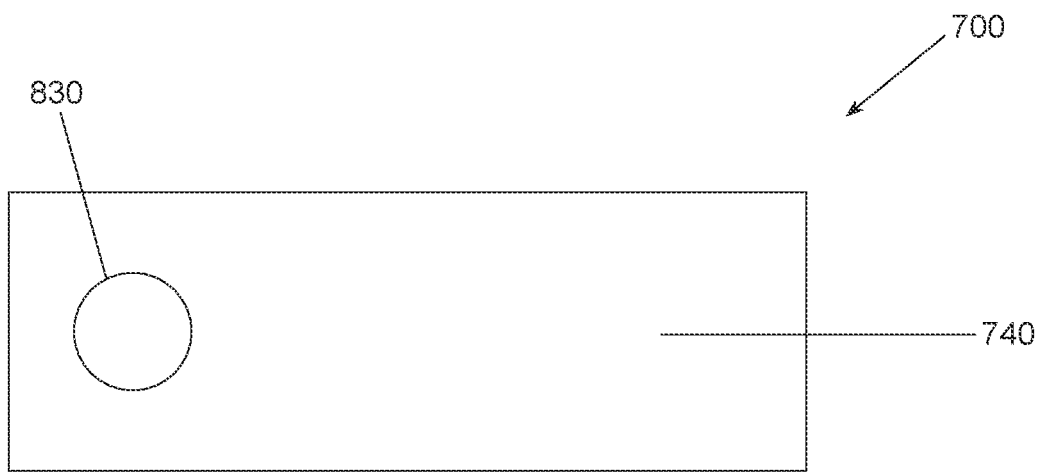
FIG. 17 is a top elevational view of the ionic oxidation refreshing system of FIG. 12.
Figure 18:
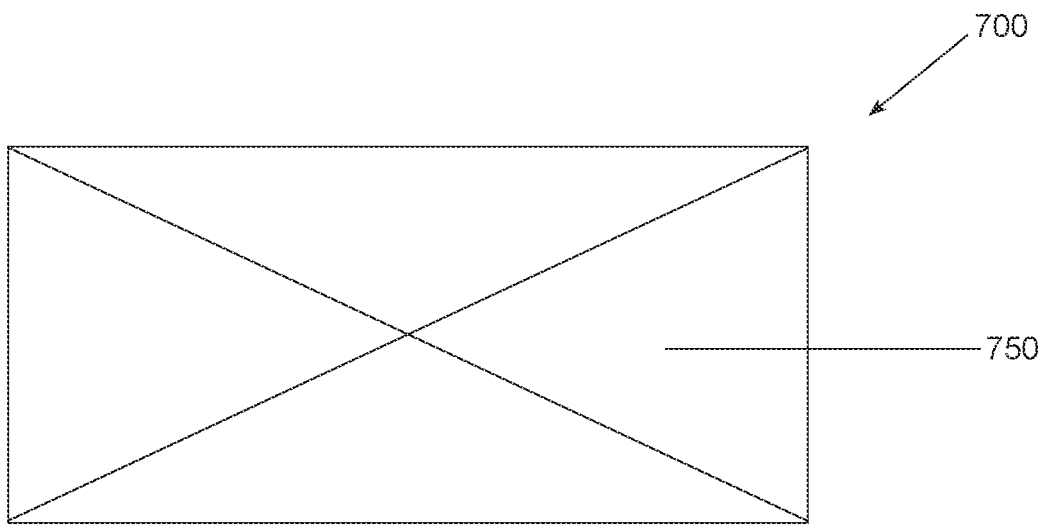
FIG. 18 is a bottom elevational view of the ionic oxidation refreshing system of FIG. 12.

FIG. 11 is a block diagram illustrating an example wired or wireless system 600 that may be used in connection with various embodiments described above/below/herein. For example, system 600 may be used as or in conjunction with one or more of the functions, processes, or methods (e.g., to store and/or execute the application or one or more software modules of the application) described herein, and may represent components of platform 510, user system(s) 530, external system(s) 540, and/or other processing devices described herein. System 600 can be a server or any conventional personal computer, or any other processor-enabled device that is capable of wired or wireless data communication. Other computer systems and/or architectures may be also used, as will be clear to those skilled in the art.

System 600 preferably includes one or more processors, such as processor 610. Additional processors may be provided, such as an auxiliary processor to manage input/output, an auxiliary processor to perform floating-point mathematical operations, a special-purpose microprocessor having an architecture suitable for fast execution of signal-processing algorithms (e.g., digital-signal processor), a slave processor subordinate to the main processing system (e.g., back-end processor), an additional microprocessor or controller for dual or multiple processor systems, and/or a coprocessor. Such auxiliary processors may be discrete processors or may be integrated with processor 610. Examples of processors which may be used with system 600 include, without limitation, the Pentium® processor, Core i7® processor, and Xeon® processor, all of which are available from Intel Corporation of Santa Clara, California.

Processor 610 is preferably connected to a communication bus 605. Communication bus 605 may include a data channel for facilitating information transfer between storage and other peripheral components of system 600. Furthermore, communication bus 605 may provide a set of signals used for communication with processor 610, including a data bus, address bus, and/or control bus (not shown). Communication bus 605 may comprise any standard or non-standard bus architecture such as, for example, bus architectures compliant with industry standard architecture (ISA), extended industry standard architecture (EISA), Micro Channel Architecture (MCA), peripheral component interconnect (PCI) local bus, standards promulgated by the Institute of Electrical and Electronics Engineers (IEEE) including IEEE 488 general-purpose interface bus (GPIB), IEEE 696/S-100, and/or the like.

System 600 preferably includes a main memory 615 and may also include a secondary memory 620. Main memory 615 provides storage of instructions and data for programs executing on processor 610, such as one or more of the functions and/or modules discussed herein. It should be understood that programs stored in the memory and executed by processor 610 may be written and/or compiled according to any suitable language, including without limitation C/C++, Java, JavaScript, Perl, Visual Basic, .NET, and the like. Main memory 615 is typically semiconductor-based memory such as dynamic random access memory (DRAM)

and/or static random access memory (SRAM). Other semiconductor-based memory types include, for example, synchronous dynamic random access memory (SDRAM), Rambus dynamic random access memory (RDRAM), ferroelectric random access memory (FRAM), and the like, including read only memory (ROM).

Secondary memory 620 may optionally include an internal medium 625 and/or a removable medium 630. Removable medium 630 is read from and/or written to in any well-known manner. Removable storage medium 230 may be, for example, a magnetic tape drive, a compact disc (CD) drive, a digital versatile disc (DVD) drive, other optical drive, a flash memory drive, and/or the like.

Secondary memory 620 is a non-transitory computer-readable medium having computer-executable code (e.g., disclosed software modules) and/or other data stored thereon. The computer software or data stored on secondary memory 620 is read into main memory 615 for execution by processor 610.

In alternative embodiments, secondary memory 620 may include other similar means for allowing computer programs or other data or instructions to be loaded into system 600. Such means may include, for example, a communication interface 640, which allows software and data to be transferred from external storage medium 645 to system 600. Examples of external storage medium 645 may include an external hard disk drive, an external optical drive, an external magneto-optical drive, and/or the like. Other examples of secondary memory 620 may include semiconductor-based memory, such as programmable read-only memory (PROM), erasable programmable read-only memory (EPROM), electrically erasable read-only memory (EEPROM), and flash memory (block-oriented memory similar to EEPROM).

As mentioned above, system 600 may include a communication interface 640. Communication interface 640 allows software and data to be transferred between system 600 and external devices (e.g. printers), networks, or other information sources. For example, computer software or executable code may be transferred to system 600 from a network server (e.g., platform 510) via communication interface 640. Examples of communication interface 640 include a built-in network adapter, network interface card (NIC), Personal Computer Memory Card International Association (PCMCIA) network card, card bus network adapter, wireless network adapter, Universal Serial Bus (USB) network adapter, modem, a wireless data card, a communications port, an infrared interface, an IEEE 1394 fire-wire, and any other device capable of interfacing system 600 with a network (e.g., network(s) 520) or another computing device. Communication interface 640 preferably implements industry-promulgated protocol standards, such as Ethernet IEEE 802 standards, Fiber Channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement customized or non-standard interface protocols as well.

Software and data transferred via communication interface 640 are generally in the form of electrical communication signals 655. These signals 655 may be provided to communication interface 640 via a communication channel 650. In an embodiment, communication channel 650 may be a wired or wireless network (e.g., network(s) 520), or any variety of other communication links. Communication channel 650 carries signals 655 and can be implemented using a variety of wired or wireless communication means including wire or cable, fiber optics, conventional phone line, cellular phone link, wireless data communication link, radio frequency ("RF") link, or infrared link, just to name a few.

Computer-executable code (e.g., computer programs, such as the disclosed application, or software modules) is stored in main memory 615 and/or secondary memory 620. Computer programs can also be received via communication interface 640 and stored in main memory 615 and/or secondary memory 620. Such computer programs, when executed, enable system 600 to perform the various functions of the disclosed embodiments as described elsewhere herein.

In this description, the term "computer-readable medium" is used to refer to any non-transitory computer-readable storage media used to provide computer-executable code and/or other data to or within system 600. Examples of such media include main memory 615, secondary memory 620 (including internal memory 625, removable medium 630, and external storage medium 645), and any peripheral device communicatively coupled with communication interface 640 (including a network information server or other network device). These non-transitory computer-readable media are means for providing executable code, programming instructions, software, and/or other data to system 600.

In an embodiment that is implemented using software, the software may be stored on a computer-readable medium and loaded into system 600 by way of removable medium 630, I/O interface 635, or communication interface 640. In such an embodiment, the software is loaded into system 600 in the form of electrical communication signals 655. The software, when executed by processor 610, preferably causes processor 610 to perform one or more of the processes and functions described elsewhere herein.

In an embodiment, I/O interface 635 provides an interface between one or more components of system 600 and one or more input and/or output devices. Example input devices include, without limitation, sensors, keyboards, touch screens or other touch-sensitive devices, biometric sensing devices, computer mice, trackballs, pen-based pointing devices, and/or the like. Examples of output devices include, without limitation, other processing devices, cathode ray tubes (CRTs), plasma displays, light-emitting diode (LED) displays, liquid crystal displays (LCDs), printers, vacuum fluorescent displays (VFDs), surface-conduction electron-emitter displays (SEDs), field emission displays (FEDs), and/or the like. In some cases, an input and output device may be combined, such as in the case of a touch panel display (e.g., in a smartphone, tablet, or other mobile device).

System 600 may also include one or more optional wireless communication components that facilitate wireless communication over a voice network and/or a data network (e.g., in the case of user system 530). The wireless communication components comprise an antenna system 670, a radio system 665, and a baseband system 660. In system 600, radio frequency (RF) signals are transmitted and received over the air by antenna system 670 under the management of radio system 665.

In an embodiment, antenna system 670 may comprise one or more antennae and one or more multiplexors (not shown) that perform a switching function to provide antenna system 670 with transmit and receive signal paths. In the receive path, received RF signals can be coupled from a multiplexor to a low noise amplifier (not shown) that amplifies the received RF signal and sends the amplified signal to radio system 665.

In an alternative embodiment, radio system 665 may comprise one or more radios that are configured to communicate over various frequencies. In an embodiment, radio system 665 may combine a demodulator (not shown) and modulator (not shown) in one integrated circuit (IC). The demodulator and modulator can also be separate components. In the incoming path, the demodulator strips away the RF carrier signal leaving a baseband receive audio signal, which is sent from radio system 665 to baseband system 660.

If the received signal contains audio information, then baseband system 660 decodes the signal and converts it to an analog signal. Then the signal is amplified and sent to a speaker. Baseband system 660 also receives analog audio signals from a microphone. These analog audio signals are converted to digital signals and encoded by baseband system 660. Baseband system 660 also encodes the digital signals for transmission and generates a baseband transmit audio signal that is routed to the modulator portion of radio system 665. The modulator mixes the baseband transmit audio signal with an RF carrier signal, generating an RF transmit signal that is routed to antenna system 670 and may pass through a power amplifier (not shown). The power amplifier amplifies the RF transmit signal and routes it to antenna system 670, where the signal is switched to the antenna port for transmission.

Baseband system 660 is also communicatively coupled with processor 610, which may be a central processing unit (CPU). Processor 210 has access to data storage areas 615 and 620. Processor 610 is preferably configured to execute instructions (i.e., computer programs, such as the disclosed application, or software modules) that can be stored in main memory 615 or secondary memory 620. Computer programs can also be received from baseband processor 660 and stored in main memory 610 or in secondary memory 620, or executed upon receipt. Such computer programs, when executed, enable system 600 to perform the various functions of the disclosed embodiments.

With reference to FIGS. 12-18, an additional embodiment of an Ionic Oxidation Refreshing (IOR) system 700 and method/process will be described. The IOR system ("system") and method introduces a new key technology needed to remove wrinkles and stains from clothing. This system 700 and method delivers a near dry-cleaning experience to users in their homes and various businesses or residential buildings as an on-site service.

Many professionals who travel need their clothing to be refreshed or cleaned during a trip. This service typically has a turnaround of one or more days, which is inconvenient for most. Traditional dry-cleaning is also a heavy process designed to remove tough stains and residues. This cleaning method is suitable for clothing that needs a deep cleaning. A more suitable solution is refreshing clothing with a process that can deliver quick results with minimal user input and resources, compared to current methods.

The system 700 and method allows people to dry-clean their clothing using a quick-cleaning solution to remove wrinkles and light stains. The method/process allows users to re-wear clothing more comfortably, instead of having to launder or dry-clean them after every use. It is especially useful for special care garments, such as dry-clean only materials that require to be brought into a professional. This advanced technology delivers a high-performance cleaning process that can maintain synthetic materials found in easy-care or performance clothing and sports gear. To meet market expectations, the quick-cleaning solution was developed to refresh previously worn clothing. This formula may also be used to lightly scent items and deliver a protective layer against odors, germs, or stains.

The system 700 includes an enclosure/housing 710 having a front 720, a rear 730, a top 740, a bottom 750, a right side 760, a left side 770, a top portion 780, a central/intermediate portion 790, and a bottom portion 800.

The front 720 includes a door 810 that provides access to a clothing/item refreshment chamber 820.

The top portion 780 along the top 740 includes a solution filling hole 830 for filling a solution reservoir 840 of a liquid delivery system 850, which also includes an electrostatic atomizer 860 of an electrostatic liquid atomization system 865.

The front 720 of the top portion 780 includes a LED push button 870 and exhaust vents 880.

A right side 760 of the bottom portion 800 includes an air intake vent 890.

A left side 770 of the bottom portion 800 includes a filter cartridge 900 of a filtering system 910.

High-speed air blades (e.g., front air blade 920, rear air blade 930) are vertically movably disposed (i.e., moving up and down to treat a clothing/item) along inner walls defining the clothing/item refreshment chamber 820.

An ultrasonic hanger 940 extending down from the top portion 780 into the clothing/item refreshment chamber 820 is used to hang clothing/item(s) 945 to be refreshed.

A high-speed centrifugal blower 950, ionization system 960, and a heater/steamer 970 are disposed in the bottom portion 800.

An additional air blade 980 is positioned in the middle of a chamber floor 990.

In one or more embodiments, the system 700 includes a camera 1000 inside the clothing/item refreshment chamber 820 with a smart AI system used for item and material detection, and/or a RFID reader 1010.

In use, the clothing/item(s) 945 is/are hung on the ultrasonic hanger 940, which is capable of agitating the clothing/item 945 at a high frequency (i.e., greater than 20 kHz) and may be used on heavier items such as jackets.

The liquid delivery system 850 includes a quick-cleaning solution, and involves/implements the following three key technologies that allow the process to work effectively: 1) the high-speed air blades 920, 930, 980 that are used to create surface tension on the fabric of the clothing 945 to smooth and stretch out any wrinkles; 2) the electrostatic liquid atomization system 865 that creates a fine mist of the quick-cleaning solution, ensuring the formula is evenly delivered onto the clothing/item 945 without over saturating any area (the air blades 920, 930, 980 help push solution droplets deep into clothing fibers and agitate the clothing/garment/item surface; this mist can be delivered within the air blade streams and sprayed inside the garment to ensure all sides are evenly treated); 3) the ionization system 960 that is comprised of a catalyzed corona discharge device, which may be similar to or the same as the corona discharge generating element 160 shown and described herein and incorporated herein, and anion filter, which may be similar to or the same as the anion diffuser/filter 180 shown and described herein and incorporated herein, generating ionized ozone inside of the air blades 920, 930, 980 for killing germs and odors, enhancing capabilities of the quick-cleaning solution.

In one or more embodiments of the system 700, the heater 970 steams water (if a direct line is connected). The heater 970 rapidly dries clothing/item 945 (e.g., clothing, boots, sports gear) inside the clothing/item refreshment chamber 820.

The high-speed centrifugal blower 950 powers the air blades 920, 930, 980 located in front and behind of the article placed inside the appliance for cleaning. The additional air blade 980 in the middle of the chamber floor 990 ensures that the clothing/item 945 placed inside is treated on the interior of the clothing/item 945 as well. In one or more embodiments of the system 700, the air stream is heated by the heater 970 to dry items or relax clothing fibers. The filtering system 910 removes any process by-products by means of the replaceable filter cartridge 900, which may be similar to or the same as the gel-based formula or liquid-based formula cartridge 170 shown and described herein and incorporated herein. At the end of a cycle, the anion ionization system 960 runs along with the filtering system 910 to remove contaminants. In one or more embodiments of the system 700, the filter cartridge 900 releases finishing surfactants, helping to restore the fit and shape of clothing, or scent molecules, that attach to clothing fibers due to a net positive surface charge.

In one or more embodiments of the system 700, the internal camera 1000 in conjunction with the smart AI system detects items and/or material. In one or more embodiments of the system 700, the RFID reader 1010 reads garment tag care instructions to adjust process parameters.

The system 100 is plugged into a wall outlet for power and connected via Wi-Fi or Bluetooth via one or more wireless devices to a smart device for wireless control and cycle progress updates.

In one or more embodiments of the system 700, an additional heavy stain removing spray is used as a spot pre-treatment on clothing/item 945, prior to starting a dry-cleaning cycle, and may include metallic nanoparticles with other agents as a cleaning catalyst.

The figures may depict exemplary configurations for the invention, which is done to aid in understanding the features and functionality that can be included in the invention. The invention is not restricted to the illustrated architectures or configurations, but can be implemented using a variety of alternative architectures and configurations. Additionally, although the invention is described above in terms of various exemplary embodiments and implementations, it should be understood that the various features and functionality described in one or more of the individual embodiments with which they are described, but instead can be applied, alone or in some combination, to one or more of the other embodiments of the invention, whether or not such embodiments are described and whether or not such features are presented as being a part of a described embodiment. Thus the breadth and scope of the present invention, especially in the following claims, should not be limited by any of the above-described exemplary embodiments.

Terms and phrases used in this document, and variations thereof, unless otherwise expressly stated, should be construed as open ended as opposed to limiting. As examples of the foregoing: the term "including" should be read as mean "including, without limitation" or the like; the term "example" is used to provide exemplary instances of the item in discussion, not an exhaustive or limiting list thereof; and adjectives such as "conventional," "traditional," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although item, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

What is claimed:

1. A method of using an ionic oxidation refreshing system, the ionic oxidation refreshing system for refreshing an odorized item comprising an enclosure with an airflow system to contact the odorized item on all sides; an ionization system that produces a positively charged ionized ozone gas mixture inside of the enclosure, killing germs, including odor-causing bacteria, viruses, molds, and fungus, and provides the odorized item inside the enclosure with a net positive charge; a filter that neutralizes and filters out any toxic by-products; an electrostatic liquid atomization system that creates a fine mist of a quick-cleaning solution, and, in conjunction with the airflow system, causes solution droplets to penetrate deep into the odorized item and agitate a surface of the odorized item, ensuring the formula is evenly delivered onto the odorized item without over saturating any area, the method comprising:
   producing an ionized ozone gas mixture inside of the enclosure with the ionization system so that the odorized item inside of the enclosure has a net positive charge;
   delivering the quick-cleaning solution with the electrostatic liquid atomization system and the airflow system so that the fine mist of the quick-cleaning solution penetrates deep into the odorized item and agitates the surface of the odorized item, ensuring the formula is evenly delivered onto the odorized item without over saturating any area;
   neutralizing and filtering out with the filter any toxic by-products resulting from surface oxidation of the odorized item by the ionized ozone gas mixture, and
   charging scent molecules with a net negative charge, opposite the net positive surface charge on the odorized item inside of the enclosure, facilitating the adherence of scent molecules to the items inside of the enclosure.

2. The method of claim 1, wherein the airflow system includes a plurality of movable high-speed air blades that deliver air blade streams of the fine mist of quick-cleaning solution, the high-speed air blades configured to create surface tension on the odorized item to smooth and stretch out any wrinkles, and the method further comprising delivering air blade streams of the fine mist of quick-cleaning solution, creating surface tension on the odorized item to smooth and stretch out any wrinkles, with the plurality of movable high-speed air blades.

3. The method of claim 2, wherein one or more of the plurality of movable high-speed air blades are vertically movable, and the method further comprising vertically moving the plurality of movable high-speed air blades.

4. The method of claim 2, wherein the airflow system is configured so that the fine mist of quick-cleaning solution is delivered within the air blade streams, and the method further comprising delivering the fine mist of quick-cleaning solution within the air blade streams with the airflow system.

5. The method of claim 1, wherein the filter is configured to neutralize and filter out any toxic by-products including one or more of ozone, nitric acid, aldehydes, and VOCs resulting from surface oxidation of the odorized item, and charging scent molecules with a net negative charge to adhere to the item inside, and the method further comprising neutralizing and filtering out any toxic by-products including one or more of ozone, nitric acid, aldehydes, and VOCs resulting from surface oxidation of the odorized item, and charging scent molecules with a net negative charge to adhere to the item inside with the filter.

6. The method of claim 1, wherein the filter includes a quick cleaning filter cartridge with an anion diffuser, and filtering out includes filtering out with the quick cleaning filter cartridge with an anion diffuser of the filter any toxic by-products resulting from surface oxidation of the odorized item by the ionized ozone gas mixture.

7. The method of claim 6, wherein the quick cleaning filter cartridge includes a catalytic oxidation polymer formula that neutralizes any remaining toxic gases, and the method further comprising neutralizing any remaining toxic gases with the catalytic oxidation polymer formula of the quick cleaning filter cartridge.

8. The method of claim 7, wherein the quick cleaning filter cartridge includes an essential oil-based fragrance that releases scent molecules, and the method further comprising releasing scent molecules with the essential oil-based fragrance of the quick cleaning filter cartridge.

9. The method of claim 8, wherein the anion diffuser is configured to charge the scent molecules with a net negative charge, to assist in the adherence of the scent molecules to the positively charged items in the enclosure, and the method further comprising charging the scent molecules with a net negative charge, to assist in the adherence of the scent molecules to the positively charged items in the enclosure, with the anion diffused.

10. The method of claim 6, wherein the quick cleaning filter cartridge includes a cartridge solution having a polymer oxidation catalyst formula with scrubbing compounds, and the method further comprising using the cartridge solution having a polymer oxidation catalyst formula with scrubbing compounds of the quick cleaning filter cartridge.

11. The method of claim 10, wherein the scrubbing compounds include one or more of manganese oxide solutions, salt solutions, sodium bicarbonate solutions, silicon dioxides, hydroxides, and peroxides, and the method further comprising using one or more of manganese oxide solutions, salt solutions, sodium bicarbonate solutions, silicon dioxides, hydroxides, and peroxides as the scrubbing compounds.

12. The method of claim 1, further including an ultrasonic hanger configured to agitate the odorized item at a frequency greater than 20 kHz, and the method further comprising agitating the odorized item at a frequency greater than 20 kHz with the ultrasonic hanger.

13. The method of claim 1, wherein the airflow system includes a high-speed centrifugal blower that powers the plurality of air blades, which are located in front, behind, and below the odorized item, and the method further comprising powering the plurality of air blades, which are located in front, behind, and below the odorized item, with the high-speed centrifugal blower of the airflow system.

14. The method of claim 1, further including an internal camera configured to detect at least one of the odorized item and a material of the odorized item, and the method further comprising detecting at least one of the odorized item and a material of the odorized item with the internal camera.

15. The method of claim 1, further including a RFID reader configured to read garment tag care instructions to adjust process parameters, and the method further comprising reading garment tag care instructions to adjust process parameters with the RFID reader.

16. The method of claim 1, further including a heater configured to rapidly dry the odorized item, and the method further comprising rapidly drying the odorized item with the heater.

17. The method of claim 1, wherein the ionizer includes a catalyzed corona discharge device containing a hybrid generating element comprising of ceramic with a quartz glass glaze coating or comprising of stainless steel with a ruthenium metal paste coating to ionize the air inside of the enclosure, and the method further comprising ionizing the air inside of the enclosure with the catalyzed corona discharge device containing a hybrid generating element comprising of ceramic with a quartz glass glaze coating or comprising of stainless steel with a ruthenium metal paste coating.

18. The method of claim 17, wherein the ionizer includes a metal catalyst, the metal catalyst being one of copper, nickel, aluminum, or other metals which have a net positive charge and release cations by oxidation, the metal catalyst also being one of adjacent to the catalyzed corona discharge device and coated on the generating element, creating a high electric flux density of charged ions and free radicals that combine with ozone to potentiate it to ionized ozone gas, with a higher oxidative power, and the method further comprising creating a high electric flux density of charged ions and free radicals that combine with ozone to potentiate it to ionized ozone gas with the metal catalyst, the metal catalyst being one of copper, nickel, aluminum, or other metals which have a net positive charge and release cations by oxidation, the metal catalyst also being one of adjacent to the catalyzed corona discharge device and coated on the generating element.

19. The method of claim 1, wherein the airflow system includes a plurality of movable high-speed air blades, and delivering the quick-cleaning solution includes delivering the quick-cleaning solution with the electrostatic liquid atomization system and the plurality of movable high-speed air blades so that surface tension is created on the odorized item to smooth and stretch out any wrinkles.

* * * * *